United States Patent [19]

Vyas et al.

[11] Patent Number: 4,866,189

[45] Date of Patent: Sep. 12, 1989

[54] INTERMEDIATES FOR THE PRODUCTION OF EPIPODOPHYLLOTOXIN AND RELATED COMPOUNDS AND PROCESSES FOR THE PREPARATION AND USE THEREOF

[75] Inventors: Dolatrai M. Vyas, Fayetteville; Paul M. Skonezny, Clay, both of N.Y.

[73] Assignee: Bristol-Myers Company, New York, N.Y.

[21] Appl. No.: 245,108

[22] Filed: Sep. 16, 1988

Related U.S. Application Data

[62] Division of Ser. No. 076,513, Jul. 22, 1987, Pat. No. 4,795,819, which is a division of Ser. No. 907,442, Sep. 15, 1986, Pat. No. 4,728,740, which is a division of Ser. No. 722,932, Apr. 12, 1985, Pat. No. 4,644,072.

[51] Int. Cl.⁴ ..................... C07D 317/70; C07C 69/75
[52] U.S. Cl. ....................................... 549/433; 560/56; 560/107; 560/227; 560/228; 560/255
[58] Field of Search ................... 549/433; 560/56, 107, 560/227, 228, 255

[56] References Cited

U.S. PATENT DOCUMENTS

| | | |
|---|---|---|
| 3,524,844 | 8/1988 | Keller-Juslen et al. ............ 536/4.1 |
| 4,294,763 | 10/1981 | Kende et al. ....................... 549/433 |
| 4,391,982 | 7/1983 | Kende et al. ....................... 549/433 |

OTHER PUBLICATIONS

W. J. Gensler & C. D. Gatsonis, *J. Org. Chem.*, 31, 4004–4008 (1966).
W. J. Gensler, et al., *J. Am. Chem. Soc.*, 82, 1714–1727 (1960).
A. S. Kende, et al., *J. Org. Chem.*, 46, 2826–2828 (1981).
W. S. Murphy and S. Wattanasin, *J. C. S. Perkin I*, 271–276 (1982).
D. Rajapaksa, *J. Am. Chem. Soc.*, 103, 6208–6209 (1981).
R. Rodrigo, *J. Org. Chem.*, 45, 4538–4540 (1980).

*Primary Examiner*—Nicky Chan
*Attorney, Agent, or Firm*—Aldo A. Algieri

[57] ABSTRACT

There is provided a novel and efficient stereoselective total synthesis of epipodoplyllotoxin and related epipodophyllotoxin compounds of the general formula

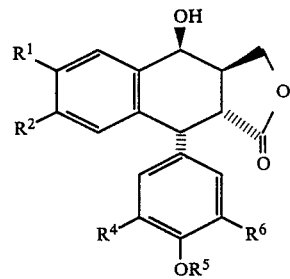

wherein $R^1$ and $R^2$ each are independently hydrogen or (lower)-alkoxy, or $R^1$ and $R^2$, taken together, is methylenedioxy; $R^4$ and $R^6$ each are independently hydrogen or (lower)alkoxy; and $R^5$ is hydrogen or a phenol-protecting group; or an acid addition salt thereof. The present invention also provides novel intermediates and processes for the preparation of said intermediates, which are then converted into known antineoplastic agents.

3 Claims, No Drawings

INTERMEDIATES FOR THE PRODUCTION OF EPIPODOPHYLLOTOXIN AND RELATED COMPOUNDS AND PROCESSES FOR THE PREPARATION AND USE THEREOF

CROSS REFERENCE TO RELATED APPLICATIONS

This application is a divisional of our prior, co-pending application Ser. No. 076,513 filed 07/22/87, now U.S. Pat. No. 4,795,819, which is div. of Ser. No. 907,442 filed 09/15/86, now U.S. Pat. No. 4,728,740, which is a div. of Ser. No. 722,932 filed 04/12/85 now U.S. Pat. No. 4,644,072.

BACKGROUND OF THE INVENTION

1. Field of the Invention

The present invention is directed to intermediates which can be converted into epipodophyllotoxin and related antineoplastic agents. More specifically, this invention relates to new and efficient total synthesis of epipodophyllotoxin, which can then be readily converted by known procedures into known antineoplastic agents. Additionally, the present invention provides processes for the preparation of such intermediates, and processes for the conversion of the intermediates into epipodophyllotoxin and related compounds.

2. Disclosure Statement

Epipodophyllotoxin (I) is the 4-hydroxy epimer of podophyllotoxin (II), which is a known lignan lactone isolated from several species of Podophyllum and possesses potent cytotoxic activity. Numerous other related compounds having the characteristic aryltetralin ring structure, either naturally occurring or derived from some naturally occurring compounds are known; some of these compounds possess antineoplastic activity, while others are useful for the conversion to compounds having such activity. Epipodophyllotoxin (I) and podophyllotoxin (II) have the structures shown below.

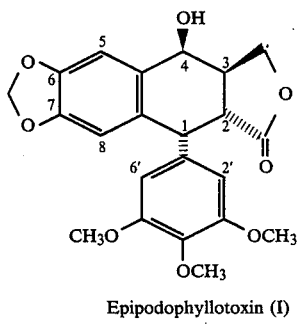

Epipodophyllotoxin (I)

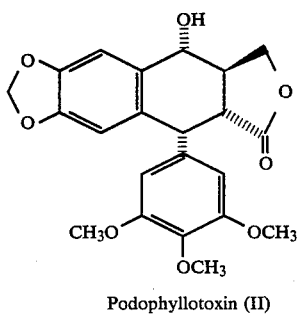

Podophyllotoxin (II)

Many of these compounds, including podophyllotoxin, have now been prepared by total synthesis.

In *J. Org. Chem.*, 31, 4004–4008 (1966), W. J. Gensler and C. D. Gatsonis describe the completion of the total synthesis of podophyllotoxin (II) through the epimerization by enolate quenching of the O-tetrahydropyranyl derivative of picropodopyllin. However, this epimerization does not proceed to completion, and separation of an about 45:55 mixture of podophyllotoxin (II) and picropodophyllin (III) is required. Picropodophyllin (III) which is the cis-lactone isomer of podophyllotoxin (II) has the structure:

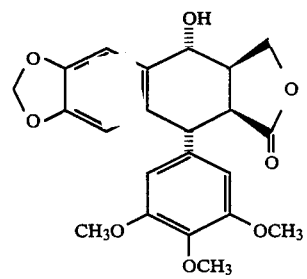

Picropodophyllin (III)

In *J. Am. Chem. Soc.*, 82, 1714–1727 (1960), W. J. Gensler et al. report the total synthesis of picropodophyllin (III) by a lengthy procedure involving 13 steps and a low overall yield. The present invention is completely different from that reported by Gensler et al. and avoids altogether the preparation of picropodophyllin (III).

In *J. Org. Chem.*, 46, 2826–2828 (1981), A. S. Kende et al. report on an improved total synthesis of podophyllotoxin (II) in 12 steps with an overall yield of 4.5% from piperonal. However, the Kende synthesis requires the preparation and then the subsequent epimerization of picropodophyllin (III) similar to the above-mentioned Gensler synthesis.

In *J. C. S. Perkin I*, 271–276 (1982), W. S. Murphy and S. Wattanasin describe an improved synthesis of the aryltetralone (IV) having the structure

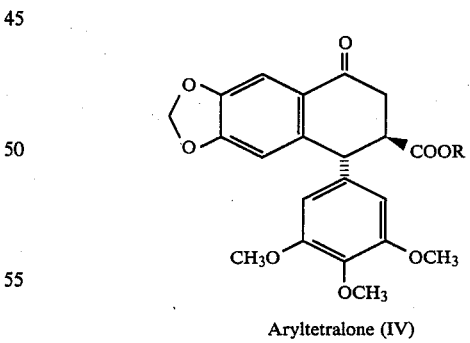

Aryltetralone (IV)

The aryltetralone (IV) is an intermediate in the synthesis of picropodophyllin (III), which is described above in *J. Am. Chem. Soc.*, 82, 1714–1727 (1960). The present invention also utilizes the aryltetralone (IV) as a starting material in the total synthesis of epipodophyllotoxin (I) described herein.

In *J. Am. Chem. Soc.*, 103, 6208–6209 (1981), D. Rajapaksa and R. Rodrigo and in *J. Org. Chem.*, 45, 4538–4540 (1980), R. Rodrigo, report a new synthesis of podophyllotoxin (II) and epipodophyllotoxin (I) which avoids the thermodynamic hurdle present in the conversion of picropodophyllin (III) to podophyllotoxin (II) as was previously described in the above-mentioned references of Gensler et al. and Kende et al. However, the Rodrigo synthesis requires the preparation of a bicyclic precursor (compound 9 in the 1980 reference), and a satisfactory yield can be achieved only by recycling procedures.

The present invention also avoids the picropodophyllin (III) intermediate and, in addition, provides a new and efficient sterospecific synthesis utilizing inexpensive chemicals, such that the new process described herein is commercially feasible.

U.S. Pat. No. 3,524,844, issued Aug. 18, 1970 to Keller-Juslen et al. describes the preparation of 4'-demethylepipodophyllotoxin-β-D-(substituted)glucosides of the formula

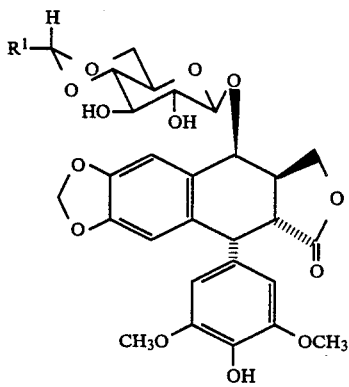

wherein, inter alia, $R^1$ is methyl (etoposide) or 2-thienyl (teniposide) from 4'-demethylepipodophyllotoxin (V) having the structure.

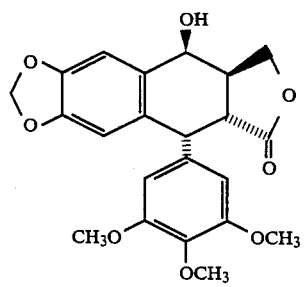

4'-Demethylepipodophyllotoxin (V)

which, in turn, is prepared from podophyllotoxin (II). The 4'-demethylepipodophyllotoxin-β-D-(substituted)-glucosides, and especially etoposide ($R^1$=methyl) and teniposide ($R^1$=2-thienyl), are antineoplastic agents which are useful in the treatment of human cancers, especially testicular cancer.

SUMMARY OF THE INVENTION

The present invention provides an efficient and stereo-specific total synthesis of epipodophyllotoxin (I) and related compounds which can readily be converted into known antineoplastic agents. Accordingly, there are provided novel intermediates having the formulae depicted in Scheme 1.

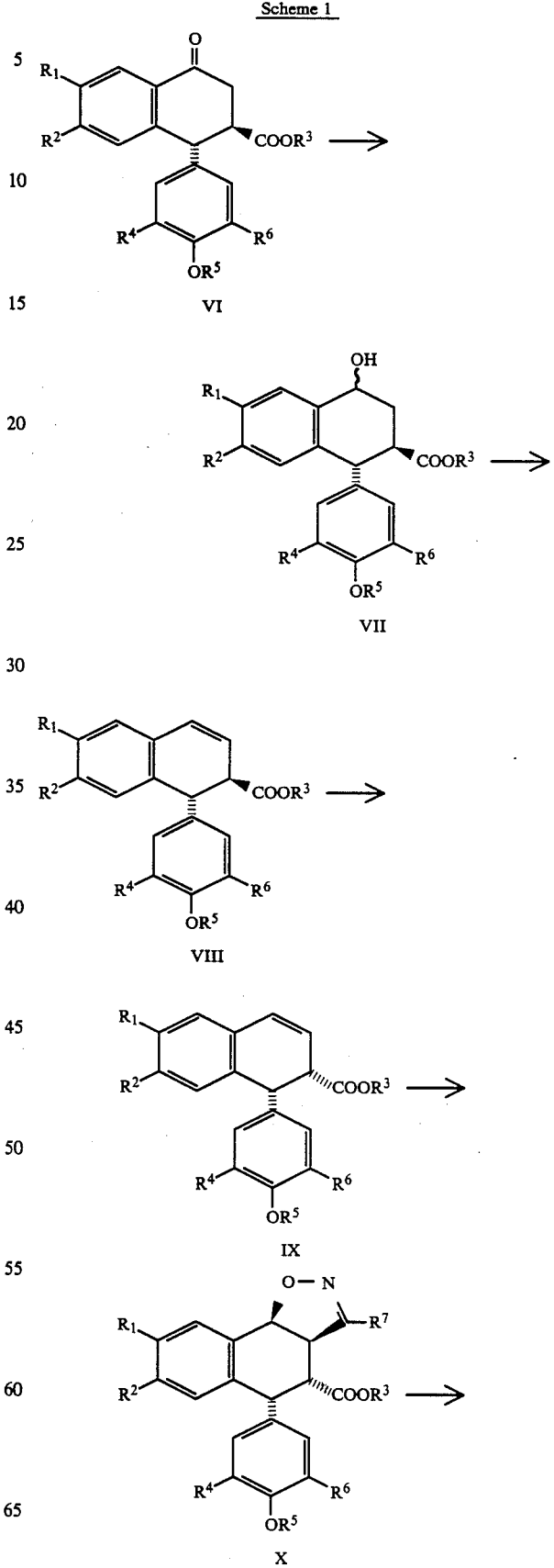

Scheme 1

-continued

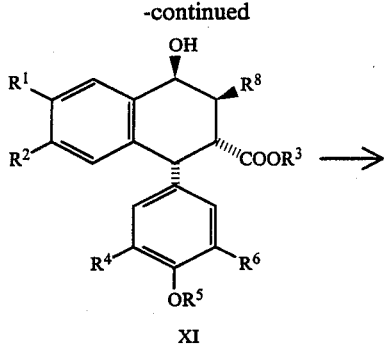

XI

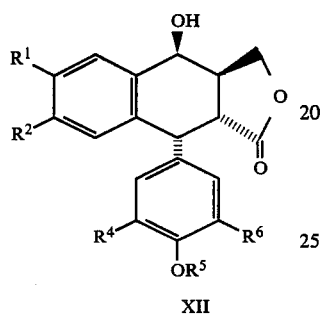

XII

-continued
Scheme 2

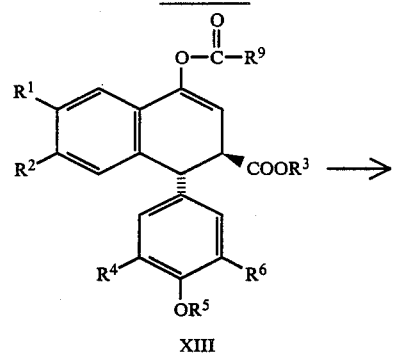

XIII

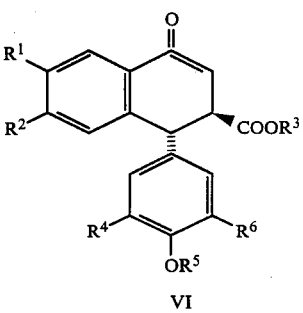

VI wherein $R^1$ and $R^2$ each are independently hydrogen or (lower)alkoxy, or $R^1$ and $R^2$, taken together, is methylenedioxy; $R^3$ is hydrogen or a carboxyl-protecting group; $R^4$ and $R^6$ each are independently hydrogen or (lower)alkoxy; $R^5$ is hydrogen or a phenol-protecting group; $R^7$ is hydrogen, halogen, (lower)alkoxycarbonyl, carboxyl, cyano, trimethylsilyl, phenylsulfonyl or phenoxycarbonyl in which the phenyl ring of $R^7$ may contain one or two substituents independently selected from (lower)alkyl, halogen, (lower)alkoxy and trifluoromethyl; and $R^8$ is cyano, aminomethyl, formyl or carbamoyl; or an acid addition salt thereof.

In another aspect of the present invention, there is provided an efficient and improved synthesis of the aryltetralones VI from the novel intermediates XIV which can be optionally isolated and having the formula depicted in Scheme 2.

Scheme 2

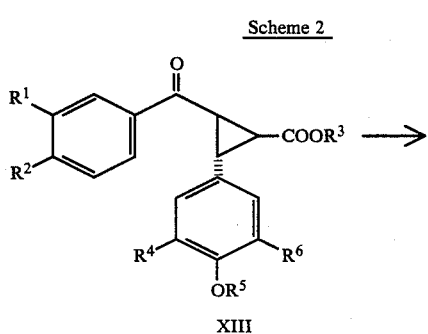

XIII wherein $R^1$, $R^2$, $R^3$, $R^4$, $R^5$ and $R^6$ are as previously defined; and $R^9$ is phenyl or (lower)alkyl optionally substituted by one or more halogen atoms selected from fluorine, chlorine and bromine.

The present invention also provides stereoselective processes for the preparation of intermediates in the total synthesis of epipodophyllotoxin and epipodophyllotoxin related derivatives. Use of the intermediates and processes of the present invention avoids the difficulties encountered in the prior art and provides a commercially feasible synthesis for useful antineoplastic agents such as etoposide and teniposide.

The terms "(lower)alkyl" and "(lower)alkoxy" as used herein and in the claims (unless the context indicates otherwise) mean unbranched or branched chain alkyl or alkoxy groups containing from 1 to 6 carbon atoms such as methyl, ethyl, propyl, isopropyl, butyl, isobutyl, t-butyl, amyl, hexyl, etc. Preferably, these groups contain from 1 to 4 carbon atoms and, most preferably, they contain 1 or 2 carbon atoms. Unless otherwise specified in the particular instance, the term "halogen" as used herein and in the claims is intended to include chlorine, fluorine, bromine and iodine. The term "acid addition salt" is intended to include the non-toxic carboxylic and phenolic acid salts, e.g. nontoxic metallic salts such as sodium, potassium, calcium and magnesium, the ammonium salt and salts with nontoxic amines, e.g. trialkylamines, procaine, dibenzylamine, pyridine, N-methylmorpholine, N-methylpiperidine and other amines which have been used to form salts of carboxylic acid and phenols.

As the compounds of the present invention may possess one or more asymmetric carbon atoms, the invention includes all of the possible enantiomeric and diastereomeric forms of the compounds of the general formulae depicted in Schemes 1 to 2 and in the claims. Mixtures of isomers can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereoisomeric salts with optically active salt-forming agents, separating the mixture into diastereomeric salts and converting the separated salts into the free compounds. The possible enantiomeric forms may also be separated by fractionation through optically active high pressure liquid chromatography columns.

If it is desired to prepare the natural (−) isomer of epipodophyllotoxin, then the synthetic (+) isomer of the present invention may be resolved by resolution methods well-known to those skilled in the art. Alternatively, the resolution may be effected at an earlier stage in the synthesis by the same general methods with one of the intermediates described herein which is capable of forming an optically active salt to produce the desired optically active (+) or (−) isomer of epipodophyllotoxin. As an example of a resolution procedure in this general class of compounds, W. J. Gensler et al. in *J. Am. Chem. Soc.*, 82, 1714–1727 (1960) described the resolution of DL-α-apopodophyllic acid to the natural optically active α-apopodophyllic acid by forming and isolating the corresponding optically active quinine salt.

Carboxyl-protecting groups which can be employed in the present invention to block or protect the carboxylic acid function are well-known to those skilled in the art and include moieties such as (lower)alkyl, phenyl(lower)alkyl, ring substituted phenyl(lower)alkyl, methoxymethyl, benzyloxymethyl, allyl, diphenylmethyl and the like. Phenol-protecting groups which can be employed in the present invention to block or protect the phenol function are also well-known to those skilled in the art and include moieties such as (lower)alkyl, phenyl(lower)alkyl, ring substituted phenyl(lower)alkyl, benzyloxycarbonyl, 2,2,2-trichloroethoxycarbonyl, methoxymethyl, allyl and the like. Other suitable protecting groups are disclosed in "Protective Groups in Organic Synthesis", Theodora W. Greene (John Wiley & Sons, 1981), Chapter 3 for phenol and Chapter 5 for carboxyl, which are hereby incorporated by reference.

DESCRIPTION OF THE INVENTION

According to one aspect of the present invention, there are provided compounds of the formula

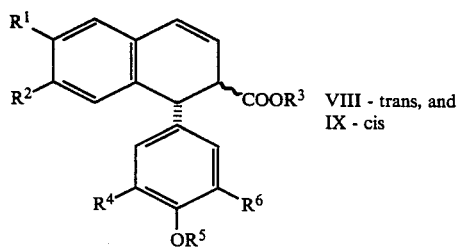

VIII - trans, and IX - cis wherein $R^1$ and $R^2$ each are independently hydrogen or (lower)alkoxy, or $R^1$ and $R^2$, taken together, is methylenedioxy; $R^3$ is hydrogen or a carboxyl-protecting group; $R^4$ and $R^6$ each are independently hydrogen or (lower)alkoxy; and $R^5$ is hydrogen or a phenol-protecting group; or an acid addition salt thereof.

In a preferred embodiment, there are provided compounds of the formula

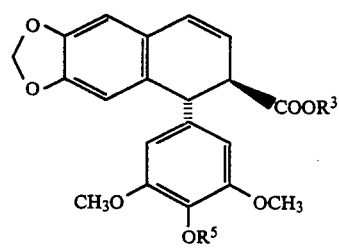

VIIIa wherein $R^3$ is hydrogen or a carboxyl-protecting group, and $R^5$ is hydrogen or a phenol-protecting group; or an acid addition salt thereof.

In another preferred embodiment, there are provided compounds of the formula

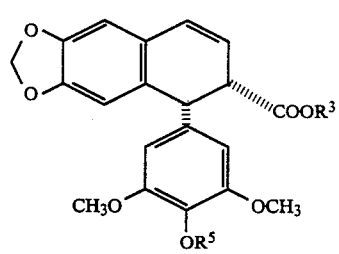

IXa wherein $R^3$ is hydrogen or a carboxyl-protecting group, and $R^5$ is hydrogen or a phenol-protecting group; or an acid addition salt thereof.

In the compounds of Formulae VIIIa and IXa, $R^3$ preferably is hydrogen, (lower)alkyl, phenyl(lower)alkyl, ring substituted phenyl(lower)alkyl or diphenylmethyl and, most preferably, is (lower)alkyl or diphenylmethyl. $R^5$ preferably is hydrogen, (lower)alkyl, phenyl(lower)alkyl, ring substituted phenyl(lower)alkyl, benzyloxycarbonyl or 2,2,2-trichloroethoxycarbonyl and, most preferably, is methyl or benzyl. The phenyl ring of $R^3$ and $R^5$ may contain one or two substituents independently selected from (lower)alkyl, halogen, (lower)alkoxy and trifluoromethyl.

The compounds of Formula VIII may be prepared from the corresponding aryltetralones of the Formula VI by reduction of the ketone radical in compounds VI or VIa and subsequent dehydration of the resulting alcohols VII or VIIa by methods wellknown to those skilled in the art, as shown in Scheme 3.

Scheme 3

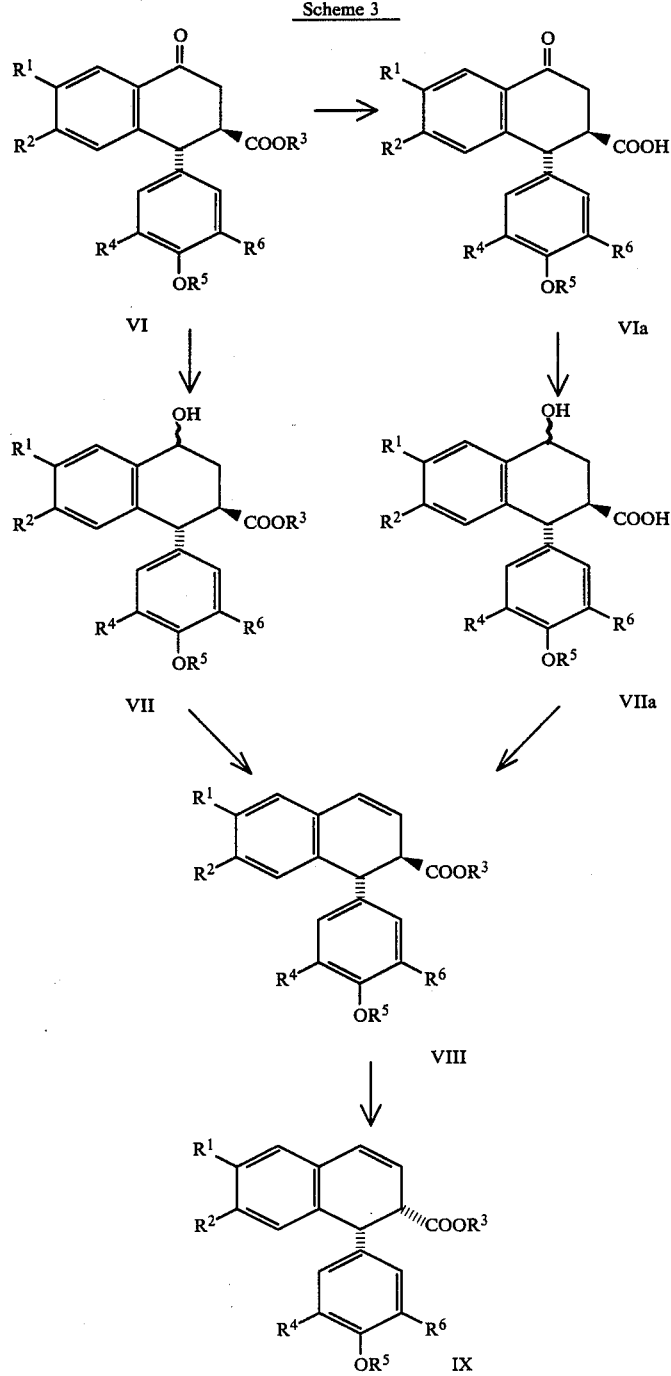

wherein $R^1$, $R^2$, $R^3$, $R^4$, $R^5$ and $R^6$ are as previously defined.

The aryltetralone starting material of the Formula VI wherein $R^1$ and $R^2$, taken together, is methylenedioxy, $R^3$ is hydrogen, $CH_3$ or $C_2H_5$, $R^4$ and $R^6$ are methoxy, and $R^5$ is methyl may be prepared by the general method described in *J. Am. Chem. Soc.*, 82, 1714–1727 (1960), W. J. Gensler et al. Starting materials of Formula VI may also be prepared by an improved procedure described in *J. C. S. Perkin I*, 271–276 (1982), W. S. Murphy and S. Wattanasin, in which $R^1$ is methoxy and $R^2$ is hydrogen, or $R^1$ and $R^2$, taken together, is methylenedioxy, $R^3$ is hydrogen or ethyl, $R^4$ and $R^6$ are hydrogen or $R^4$ and $R^6$ are methoxy, and $R^5$ is methyl. Alternatively, the starting materials of the general Formula VI may be prepared by the new and improved procedure illustrated in more detail in the disclosure and examples of the present invention.

According to one reaction route, when it is desired to change the $R^3$ carboxyl-protecting group, the aryltetralone VI is first hydrolyzed by conventional methods, such as acid or base hydrolysis, and preferably by base hydrolysis, for example, potassium hydroxide. The resulting acid VIa is then subjected to selective reducing conditions to effect the reduction of the ketone radical to the alcohol VIIa. The reduction may be accomplished by catalytic hydrogenation employing hydrogenation catalysts such as palladium, platinum, Raney nickel or ruthenium, being optionally supported on a conventional carrier such as carbon, diatomaceous earth, etc., in non-reducible inert solvents such as water, methanol, ethanol or ethyl acetate. Hydrogenation is preferably conducted at room temperature and at atmospheric or slightly elevated pressure. More preferably, the aryltetralone VIa is reduced in a suitable solvent with a selective reducing agent, e.g., sodium borohydride, sodium cyanoborohydride, zinc borohydride, sulfurated sodium borohydride ($NaBH_2S_3$), lithium borohydride, disiamylborane, ammonia borane, t-butylamine borane, pyridine borane, lithium tri-s-butylborohydride, or other similar reducing agents which will not reduce the carboxylic acid radical. The alcohol VIIa which is produced is then subjected to standard dehydration conditions with a small amount of organic or mineral acid such as p-toluenesulfonic acid or sulfuric acid to give the trans-olefin VIII, wherein $R^3$ is hydrogen. The reaction is carried out in a suitable inert organic solvent, e.g., toluene, benzene, ether or methylene chloride, in the presence of a drying agent, e.g. $Na_2SO_4$, $MgSO_4$, molecular sieves, etc., or preferably, the water which is produced is azeotropically removed with a Dean-Stark trap or similar apparatus. The trans-olefin VIII, wherein $R^3$ is hydrogen, may then be esterified in the usual manner with a suitable carboxyl-protecting group and preferably with benzhydryl.

It should be appreciated by those skilled in the art that the alcohol VIIa may form the corresponding lactone XV in the dehydration reaction. The production of the lactone XV will depend on the relative stereochemical configuration of the hydroxyl and carboxyl radicals of the alcohol VIIa which are used in the dehydration reaction.

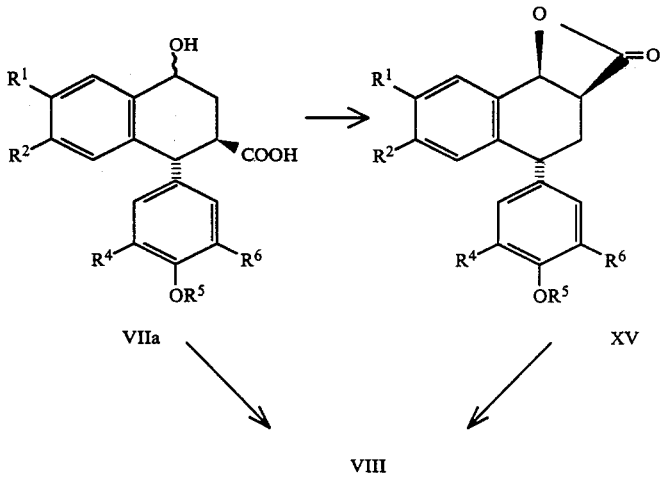

The trans-olefin VIII, wherein $R^3$ is a carboxyl-protecting group, may then be prepared directly by the addition of an alcohol, for example, benzhydryl alcohol, to the dehydration reaction employing the lactone XV.

In one specific example wherein $R^1$ and $R^2$, taken together, is methylenedioxy, $R^4$ and $R^6$ are methoxy and $R^5$ is methyl, the alcohol VIIb was dehydrated and then esterified in the usual manner with benzhydryl alcohol to produce the trans-olefin VIIIa.

In another specific example, the lactone XVa was isolated from one of the dehydration reactions employing the corresponding alcohol VIIb. Treatment of the resulting lactone XVa with benzhydryl alcohol under standard acidic dehydration conditions produced the desired trans-olefin VIIIa as shown below.

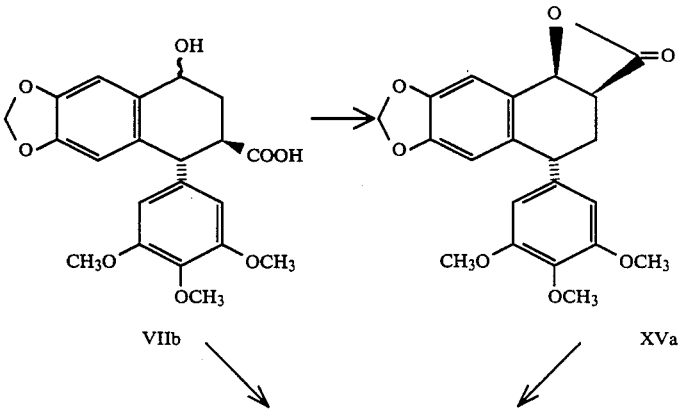

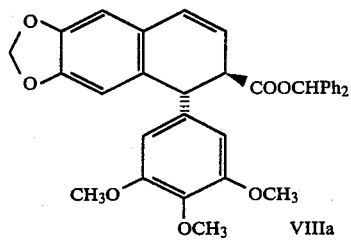

VIIIa

In an alternate reaction route, when it is desired to retain the same $R^3$ carboxyl-protecting group, the selective reduction of the aryltetralone VI may be carried out by catalytic hydrogenation employing hydrogenation catalysts such as palladium, platinum, Raney nickel or ruthenium, being optionally supported on a conventional carrier such as carbon, diatomaceous earth, etc., in non-reducible inert solvents such as methanol, ethanol or ethyl acetate. Hydrogenation is preferably conducted at room temperature and at atmospheric or slightly elevated pressure. More preferably, the aryltetralone VI is reduced in a suitable solvent with a selective reducing agent, e.g., sodium borohydride, sodium cyanoborohydride, zinc borohydride, sulfurated sodium borohydride ($NaBH_2S_3$), disiamylborane, diborane, ammonia borane, t-butylamine borane, pyridine borane, lithium tri-s-butylborohydride, or other similar reducing agents which will not reduce the carboxylic ester radical. The alcohol VII which is produced is then subjected to standard dehydration conditions with a small amount of organic or mineral acid such as p-toluenesulfonic acid or sulfuric acid to produce the trans-olefin VIII, wherein $R^3$ is a carboxyl-protecting group. The reaction is carried out in a suitable inert organic solvent, e.g. toluene, benzene, ether or methylene chloride, in the presence of a drying agent, e.g. $Na_2SO_4$, $MgSO_4$, molecular sieves, etc., or preferably, the water which is produced is azeotropically removed with a Dean-Stark trap or similar apparatus.

Conversion of the trans-olefin VIII to the cis-olefin IX may be effected by the epimerization of the carboxylic ester radical. This epimerization is usually carried out in an inert organic solvent such as THF and at low temperatures from about $-78°$ C. to $-20°$ C. and preferably at about $-78°$ C. while employing a strong base such as lithium hydride, potassium bis(trimethylsilyl)amide, lithium diisopropylamide or lithium bis(trimethylsilyl)amide. The resulting anion is then quenched with acid, for example, mineral acids such as hydrochloric acid, sulfuric acid or the like, to produce stereoselectively the cis-olefin IX.

In another aspect of the present invention, there are provided compounds of the formula

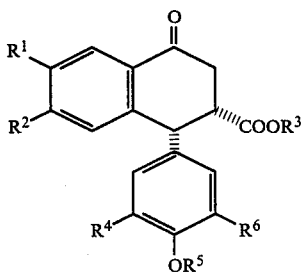

XVI wherein $R^1$ and $R^2$ each are independently hydrogen or (lower)alkoxy, or $R^1$ and $R^2$, taken together, is methylenedioxy; $R^3$ is hydrogen or a carboxyl-protecting group; $R^4$ and $R^6$ each are independently hydrogen or (lower)alkoxy; and $R^5$ is hydrogen or a phenol-protecting group; or an acid addition salt thereof.

In a preferred embodiment, there are provided compounds of the formula

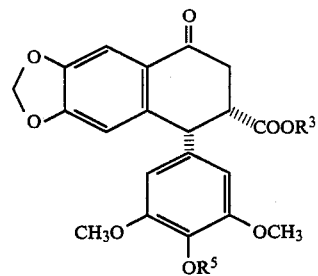

XVIa wherein $R^3$ is hydrogen or a carboxyl-protecting group, and $R^5$ is hydrogen or a phenol-protecting group; or an acid addition salt thereof.

In a more preferred embodiment, there are provided compounds of the Formula XVIa wherein $R^3$ is (lower)alkyl or diphenylmethyl and $R^5$ is methyl or benzyl.

The cis-aryltetralone of Formula XVI may be prepared by the epimerization of the corresponding trans-aryltetralones VI. Compounds of Formula XVI are then reduced and dehydrated to produce cis-olefins of Formula IX according to Reaction Scheme 4.

Scheme 4

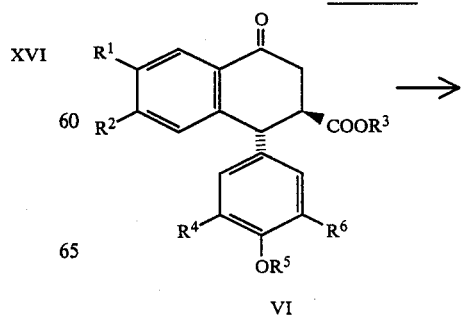

VI

-continued
Scheme 4

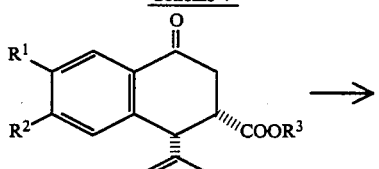

XVI

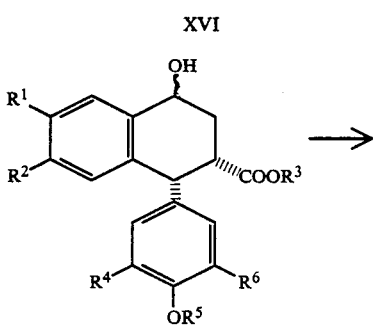

XVII

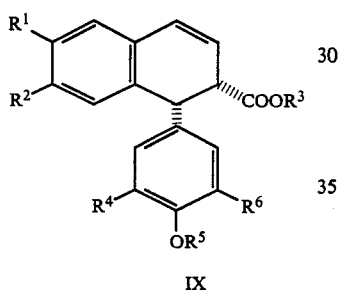

IX

The starting aryltetralone VI, with the ester radical in the relative trans configuration, is epimerized to the cis-aryltetralone XVI at low temperatures from about −70° C. to −20° C. and preferably at about −78° C. by enol quenching utilizing a strong base such as lithium hydride, potassium bis(trimethylsilyl)amide, lithium diisopropylamide or lithium bis(trimethylsilyl)amide in an inert organic solvent such as THF and then adding a mineral acid, for example, hydrochloric acid.

The resulting cis-aryltetralone XVI may then be subjected to selective reducing conditions to effect the reduction of the ketone radical to the alcohol XVII wherein $R^3$ is a carboxyl-protecting group. The reduction may be carried out by catalytic hydrogenation employing hydrogenation catalysts such as palladium, platinum, Raney nickel or ruthenium, being optionally supported on a conventional carrier such as carbon, diatomaceous earth, etc., in non-reducible inert solvents such as water, methanol, ethanol or ethyl acetate. Hydrogenation is preferably conducted at room temperature and at atmospheric or slightly elevated pressure. More preferably, the aryltetralone XVI is reduced in a suitable solvent with a selective reducing agent, e.g. sodium borohydride, sodium cyanoborohydride, zinc borohydride, sulfurated sodium borohydride (NaBH$_2$S$_3$), disiamylborane, diborane, ammonia borane, t-butylamine borane, pyridine borane, lithium tri-s-butylborohydride, or other similar reducing agents which will not reduce, hydrolyze nor epimerize the carboxylic ester radical. The alcohol XVII which is produced may then be subjected to standard dehydration conditions with a small amount of organic or mineral acid such as p-toluenesulfonic acid or sulfuric acid to produce the cis-olefin IX, wherein $R^3$ is a carboxyl-protecting group. The reaction is carried out in a suitable inert organic solvent, e.g., toluene, benzene, ether or methylene chloride, in the presence of a drying agent, e.g. Na$_2$SO$_4$, MgSO$_4$, molecular sieves, etc., or preferably, the water which is produced is azeotropically removed with a Dean-Stark trap or similar apparatus.

According to another reaction route, the cis-aryltetralone XVI is reduced in a suitable solvent with a selective reducing agent, preferably lithium borohydride, to give the alcohol XIIa and/or the lactone having the formula XVIII.

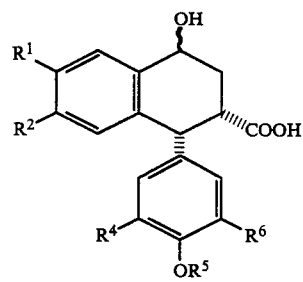

XIIa

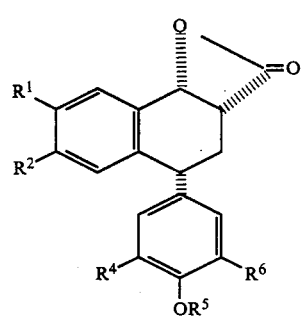

XVIII

It should be appreciated by those skilled in the art that the alcohol XIIa may form the corresponding lactone XVIII in the reduction and workup. The amount of lactone XVIII isolated from the reaction will depend on the relative stereochemical configuration of the hydroxyl and carboxyl radicals of the alcohol XIIa which was produced in the reduction. In the specific example wherein $R^1$ and $R^2$, taken together, is methylenedioxy, $R^4$ and $R^6$ are methoxy and $R^5$ is methyl, the lactone XVIIIa was the preferred product isolated from the reaction mixture.

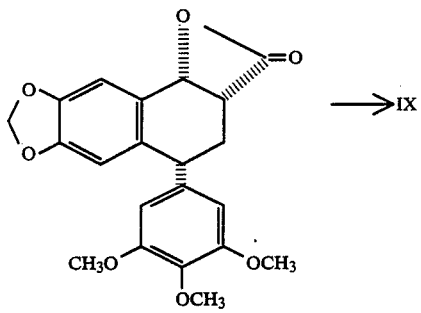

The resulting lactone XVIIIa may then be treated with an alcohol, and preferably with benzhydryl alcohol, under standard acidic dehydration conditions, as described above for lactone XVa, to produce the desired cis-olefin IX wherein $R^3$ is a carboxyl-protecting group.

According to another aspect of the present invention, there are provided compounds of the formula

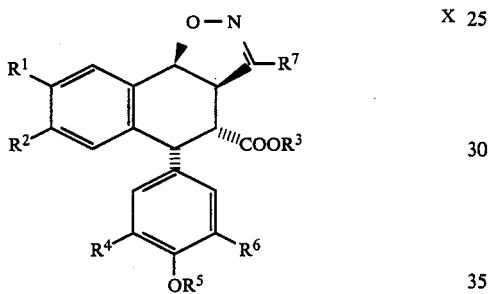

wherein $R^1$ and $R^2$ each are independently hydrogen or (lower)alkoxy, or $R^1$ and $R^2$, taken together, is methylenedioxy; $R^3$ is hydrogen or a carboxyl-protecting group; $R^4$ and $R^6$ each are independently hydrogen or (lower)alkoxy; $R^5$ is hydrogen or a phenol-protecting group; and $R^7$ is hydrogen, halogen, (lower)alkoxycarbonyl, carboxyl, cyano, trimethylsilyl, phenylsulfonyl or phenoxycarbonyl in which the phenyl ring of $R^7$ may contain one or two substituents independently selected from (lower)alkyl, halogen, (lower)alkoxy and trifluoromethyl.

In a preferred embodiment, there are provided compounds of the formula

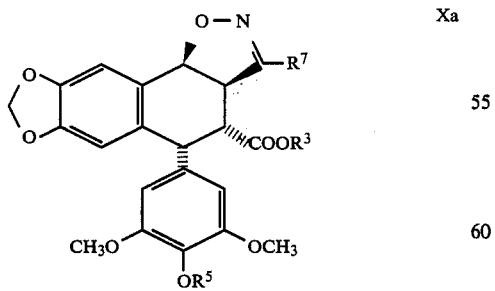

wherein $R^3$ is hydrogen or a carboxyl-protecting group; $R^5$ is hydrogen or a phenol-protecting group; and $R^7$ is hydrogen, halogen, (lower)alkoxycarbonyl, carboxyl, cyano, trimethylsilyl, phenylsulfonyl or phenoxycarbonyl in which the phenyl ring of $R^7$ may contain one or two substituents independently selected from (lower)alkyl, halogen, (lower)alkoxy and trifluoromethyl.

In a more preferred embodiment, there are provided compounds of the Formula Xa wherein $R^3$ is hydrogen, (lower)alkyl or diphenylmethyl; $R^5$ is methyl or benzyl; and $R^7$ is bromine or chlorine.

The compounds of Formula X may be prepared from the corresponding cis-olefins of the Formula IX by employing a [3+2] cycloaddition reaction as shown in Scheme 5.

Scheme 5

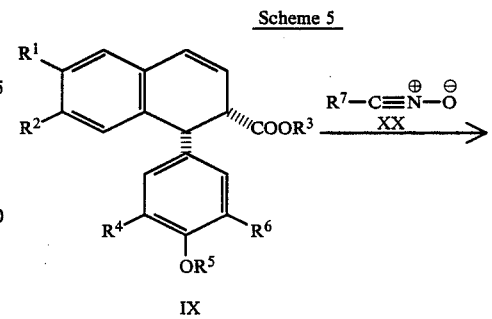

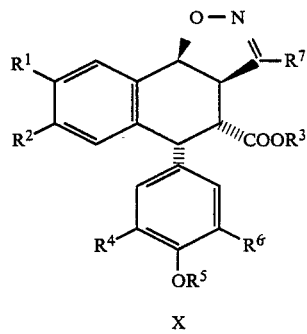

The cis-olefin IX is reacted with at least one equivalent of a substituted nitrile oxide of the formula XX at about $-20°$ C. to refluxing temperatures in an inert solvent (aqueous or organic, or mixed aqueous-organic) such as water, $C_1$-$C_6$ alcohols, ethyl acetate, dioxane, tetrahydrofuran, acetone, nitromethane, methylene chloride or chloroform to give the isoxazole adduct X. Although the solvent and temperature of the reaction are not critical, it is preferred, when $R^7$ is halogen, that the reaction be conducted near the refluxing temperature of the solvent, for example, acetone or ethyl acetate.

It is preferred to use an excess amount of the nitrile oxide XX in the above 1,3-dipolar cycloaddition reaction, and more preferably, an excess of 3 equivalents is used. It is also preferred to generate the nitrile oxide XX in situ from the corresponding formaldoxime XIX in the presence of an inorganic base such as $KHCO_3$ or $Na_2CO_3$ or a trisubstituted amine such as triethylamine or pyridine as shown below:

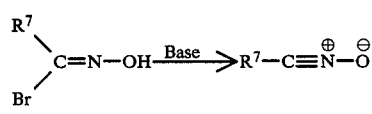

XIX                  XX

For the preparation of Compound XXa, wherein $R^7$ is bromo, the bromonitrile oxide is generated from dibromoformaldoxime XIX wherein $R^7$ is bromine as described in *Tetrahedron Letters* 21, 229-230 (1980), or more preferably by the modified procedure described herein in Example 20, Step A. Other nitrile oxides of the formula XX wherein $R^7$ is hydrogen; ethoxycarbonyl, carboxyl and cyano; trimethylsilyl; and phenylsulfonyl may be prepared by the general procedures described in *Tetrahedron Letters*, 24, 1815-1816 (1983); *J. Org. Chem.*, 48, 366-372 (1983); Synthesis, 719 (1982); and *J. Org. Chem.*, 48, 1796-1800 (1983), respectively, and references therein.

In the specific example with Compound X, wherein $R^1$ and $R^2$, taken together, is methylenedioxy; $R^4$ and $R^6$ are methoxy; $R^5$ is methyl; $R^7$ is bromine; and $R^3$ is diphenylmethyl, deblocking of the carboxyl-protecting group with dry HCl in an inert organic solvent such as nitromethane readily gave crystalline isoxazole acid Xc, wherein $R^3$ is hydrogen and $R^7$ is chlorine. This particular deblocking procedure of a compound of Formula X resulted in halogen displacement wherein the bromine radical of $R^7$ in the isoxazole ring was replaced by chlorine. When it is desired to retain the bromine radical of $R^7$, then the deblocking procedure is preferably carried out with trifluoroacetic acid as is demonstrated herein for the preparation of the isoxazole acid Xd.

The stereospecific construction of the isoxazole ring in Compound X which was produced by the approach of the substituted nitrile oxide XX with diastereoface selection to the β face of the cis-olefin IX, can be readily determined by $^1$H NMR spectroscopy. However, in order to provide additional evidence of the regiospecific and stereospecific nature of the present invention, the [3+2] cycloaddition reaction was repeated with the trans-olefin VIIIb as shown below:

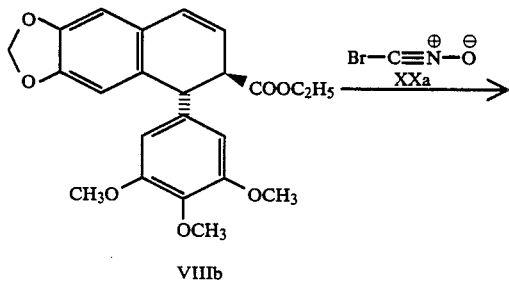

VIIIb

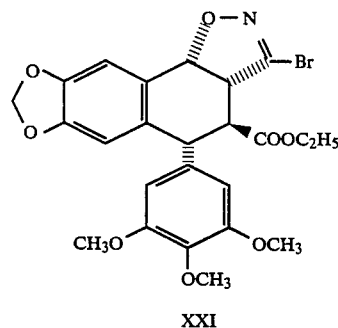

XXI

The isolation of Compound XXI containing the opposite stereochemistry in the attachment of the isoxazole ring confirms that the process of the invention described herein for the preparation of Compound X is a highly stereoselective process for producing the desired regiospecificity required for the efficient synthesis of epipodophyllotoxin and epipodophyllotoxin-related derivatives.

According to a further aspect of the present invention, there are provided compounds of the formula

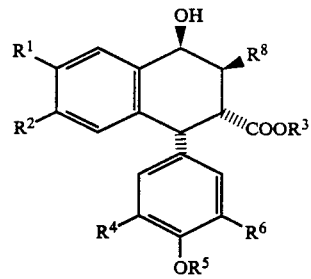

wherein $R^1$ and $R^2$ each are independently hydrogen or (lower)alkoxy, or $R^1$ and $R^2$, taken together, is methylenedioxy; $R^3$ is hydrogen or a carboxyl-protecting group; $R^4$ and $R^6$ each are independently hydrogen or (lower)alkoxy; $R^5$ is hydrogen or a phenol-protecting group; and $R^8$ is cyano, aminomethyl, formyl or carbamoyl; or an addition salt thereof.

In a preferred embodiment, there are provided compounds of the formula

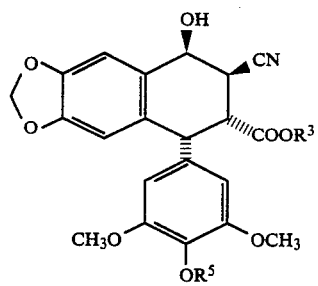

wherein $R^3$ is hydrogen or a carboxyl-protecting group; and $R^5$ is hydrogen or a phenol-protecting group; or an acid addition salt thereof.

In a more preferred embodiment, there are provided compounds of the Formula XIa wherein $R^3$ is hydrogen, (lower)alkyl or diphenylmethyl and $R^5$ is methyl or benzyl; or an acid addition salt thereof.

In another preferred embodiment, there are provided compounds of the formula

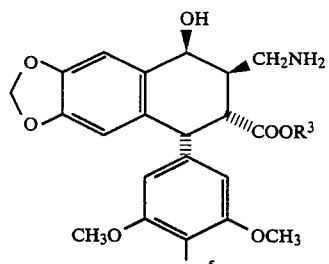

wherein $R^3$ is hydrogen or a carboxyl-protecting group; and $R^5$ is hydrogen or a phenol-protecting group; or an addition salt thereof.

In a more preferred embodiment, there are provided compounds of the Formula XIb wherein $R^3$ is hydrogen, (lower)alkyl or diphenylmethyl and $R^5$ is methyl or benzyl; or an addition salt thereof.

The epipodophyllotoxin and epipodophyllotoxin related derivatives of Formula XII may be prepared from the corresponding isoxazole compounds of Formula X by the sequence described in Scheme 6.

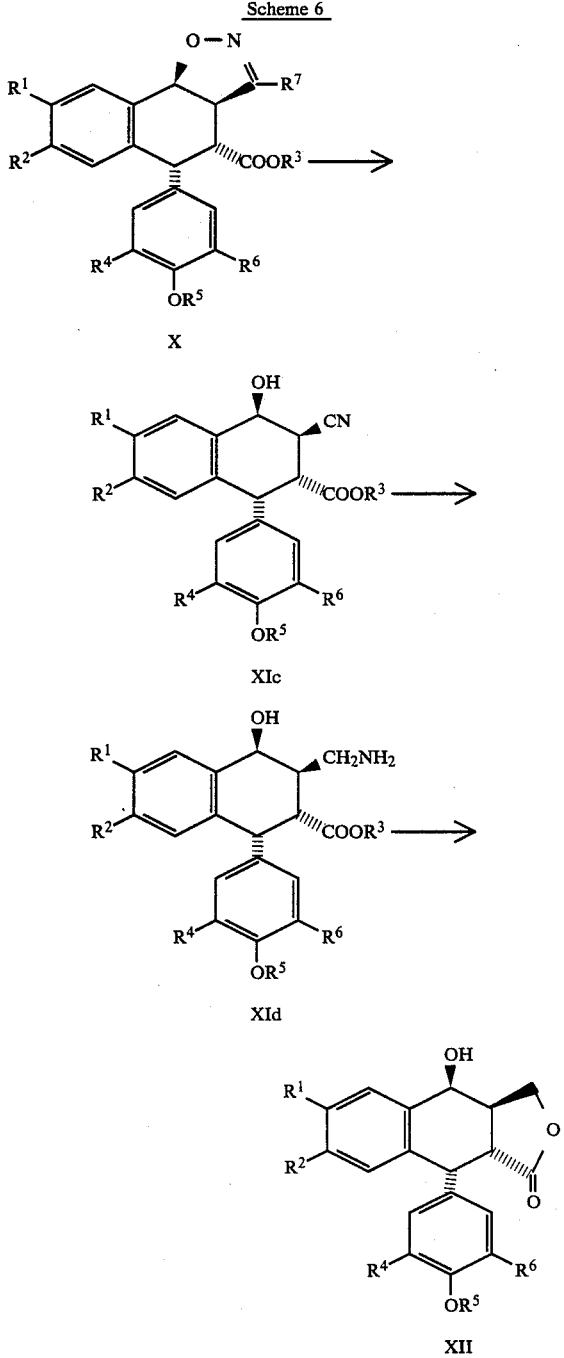

Scheme 6

Compounds of the Formula X are subjected to reaction conditions to provide N—O bond heterolysis. The conditions for cleaving the isoxazole ring will normally vary depending on the $R^7$ substituent and whether $R^3$ is hydrogen or a carboxyl-protecting group. For example, when $R^7$ is trimethylsilyl, thermal rearrangement followed by hydrolysis according to the general procedures described in *Heterocycles*, 20, 511–518 (1983) will produce compounds of the Formula XIc. When $R^7$ is alkoxycarbonyl, phenylcarbonyl or cyano, hydrolysis to compound X wherein $R^7$ is carboxyl followed by decarboxylation according to the general procedures described in *J. Org. Chem.*, 48, 366–372 (1983) will also provide compounds of the Formula XIc. In the case where $R^7$ is phenylsulfonyl and $R^3$ is hydrogen or a carboxyl-protecting group, selective reduction with, for example, sodium borohydride or 2% sodium amalgam according to the general procedures described in *J. Org. Chem.*, 49, 123–125 (1984) and *J. Am. Chem. Soc.*, 101, 1319 (1979) will produce compounds of the Formula XIc. Additionally, if a stronger reducing agent such as lithium aluminum hydride is employed with a compound of Formula X wherein $R^3$ is hydrogen, then the resulting cyano compound of Formula XIc may, without isolation, be further reduced to produce the aminomethyl compound of Formula XId. Furthermore, it has been found that the isoxazole of Formula X wherein $R^7$ is bromo may be reduced to Compound XIc with tributyltin hydride in the presence of a free radical initiator such as 2,2'-azobisisobutyronitrile. More preferably, reduction of Compounds X wherein $R^7$ is chlorine or bromine is carried out by catalytic hydrogenation. The reduction is preferably conducted at initial pressures of about 40–50 psi of hydrogen in the presence of a catalyst such as Raney nickel, platinum oxide, palladium on carbon or nickel boride in a non-reducing solvent, e.g. alcohols, ethyl acetate, water or the like, or mixtures thereof. When the reduction is carried out with a compound of Formula X wherein $R^3$ is other than hydrogen, then the pH of the solution may be adjusted to prevent the possible epimerization of the carboxyl group by adding a suitable buffering agent such as boric acid or other similar mild buffering acid. If Compound X wherein $R^3$ is hydrogen is used, then the reduction is less sensitive to the reaction conditions and the buffering agent may be omitted.

Compounds of the Formula XIc wherein $R^3$ is hydrogen or a carboxyl-protecting group are then selectively reduced to effect the reduction of the cyano radical to the aminomethyl compounds of the Formula XId. When $R^3$ is a carboxyl-protecting group, the reduction may be carried out by catalytic hydrogenation employing hydrogenation catalysts such as platinum oxide or Raney nickel in non-reducible inert solvents such as water, methanol, ethanol or ethyl acetate, or mixtures thereof. Hydrogenation is preferably conducted at room temperature and at atmospheric or slightly elevated pressure. Alternatively, the reduction may be carried out with selective reducing agents such as diborane in tetrahydrofuran or other similar reducing agents which will not reduce nor epimerize the carboxylic ester radical. The resulting compounds of Formula XId wherein $R^3$ is a carboxyl-protecting group may then be removed under non-epimerizing conditions, e.g. hydrogenolysis or acid hydrolysis.

More preferably, the reduction of the cyano radical of Compounds XIc wherein $R^3$ is hydrogen is carried out by catalytic hydrogenation employing hydrogenation catalysts such as platinum oxide or Raney nickel in non-reducible inert solvents such as methanol, ethanol, ethyl acetate, methylene chloride or mixtures thereof. Hydrogenation is preferably conducted at room temperature and at atmospheric or slightly elevated pressure. Most preferably, the reduction is carried out with lithium aluminum hydride in a suitable solvent such as tetrahydrofuran. The resulting product of Formula XId wherein $R^3$ is hydrogen may, if desired, be isolated in the form of an addition salt such as an acetic acid salt.

The aminomethyl compounds of Formula XId wherein $R^3$ is hydrogen are then cyclized by diazotization of the primary amine, and preferably with sodium nitrite or i-amyl nitrite in an aqueous acidic medium such as aqueous acetic acid or aqueous trifluoroacetic acid. The cyclization proceeds directly to the desired lactones of the Formula XII having the correct relative stereochemistry of epipodophyllotoxin and podophyllotoxin.

Compounds of the Formula XIc may, if desired, be selectively converted to compounds of the Formula XI wherein $R^8$ is formyl by methods well-known to those skilled in the art such as catalytic hydrogenation with Raney nickel in the presence of sodium hypophosphite in aqueous acetic acid or zinc in acetic acid. The compounds of Formula XI wherein $R^8$ is formyl and $R^3$ is hydrogen may then be selectively reduced to the alcohol epipodophyllic acid which may be converted to epipodophyllotoxin and related compounds by the method described in *J. Am. Chem. Soc.*, 103, 6208–6209 (1981).

Compounds of the Formula XIc may, if desired, be selectively converted to compounds of the Formula XI wherein $R^8$ is carbamoyl with e.g., hydrogen peroxide. The compounds of Formula XI wherein $R^8$ is carbamoyl and $R^3$ is hydrogen may then be selectively reduced with e.g., lithium aluminum hydride, to provide compounds of the Formula XId wherein $R^3$ is hydrogen, which are converted to epipodophyllotoxin and related compounds by the methods described herein.

In a more preferred reaction pathway, the compounds of Formula XIb need not be isolated and may be reacted further to the desired epipodophyllotoxin (I) and related compounds. Thus, for example, the compound of Formula XIa wherein $R^5$ is methyl and $R^3$ is hydrogen is first treated with a reducing agent such as lithium aluminum hydride to effect reduction of the cyano radical. After the evaporation of the solvent, the resulting crude product of Formula XIb is then treated with a solution of sodium nitrite to effect diazotization and subsequent lactonization to produce the desired epipodophyllotoxin (I), as shown below:

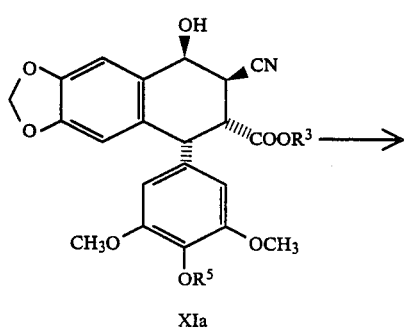

XIa

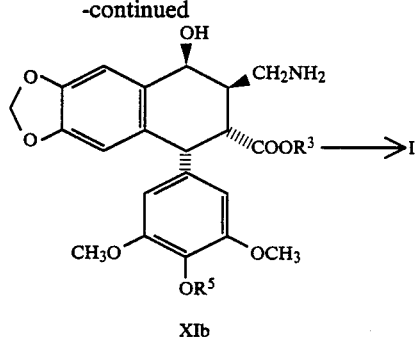

XIb

In a still more preferred reaction pathway, the compounds of Formulae XIa and XIb need not be isolated and may be treated further to the desired epipodophyllotoxin (I). Thus, for example, the compound of Formula Xa wherein $R^5$ is methyl, $R^3$ is hydrogen and $R^7$ is chlorine is sequentially treated with nickel boride and then platinum oxide at room temperature under an initial hydrogen pressure of about 40–50 psi. The resulting crude product of Formula XIb, without further isolation and purification, is treated with diazotizing agent and preferably with sodium nitrite in an acid medium such as aqueous acetic acid to give the desired epipodophyllotoxin (I).

In still another aspect of the present invention, there are provided compounds of the formula

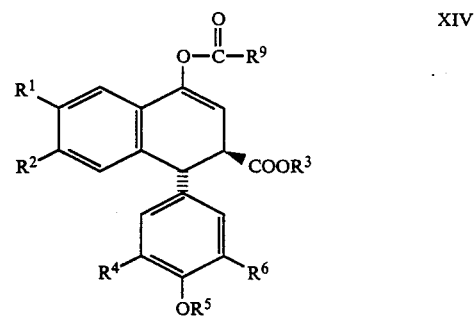

XIV wherein $R^1$ and $R^2$ each are independently hydrogen or (lower)alkoxy, or $R^1$ and $R^2$, taken together, is methylenedioxy; $R^3$ is hydrogen or a carboxyl-protecting group; $R^4$ and $R^6$ each are independently hydrogen or (lower)alkoxy; $R^5$ is hydrogen or a phenol-protecting group; and $R^9$ is phenyl or (lower)alkyl optionally substituted by one or more halogen atoms selected from fluorine, chlorine and bromine.

In a preferred embodiment, there are provided compounds of the formula

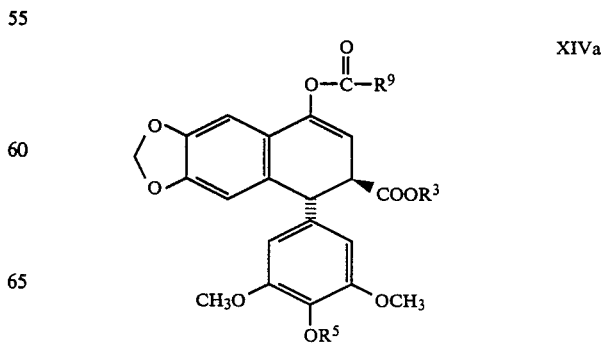

XIVa wherein $R^3$ is hydrogen or a carboxyl-protecting group; $R^5$ is hydrogen or a phenol-protecting group; and $R^9$ is phenyl or (lower)alkyl optionally substituted by one or more halogen atoms selected from fluorine, chlorine and bromine.

In a still more preferred embodiment, there are provided compounds of the Formula XIVa wherein $R^3$ is diphenylmethyl; $R^5$ is methyl or benzyl; and $R^9$ is methyl.

The compounds of Formula XIV may be prepared from the corresponding compounds of the Formula XIII by an efficient and improved cyclization procedure. The cyclopropane compounds XIII are themselves prepared from the readily available chalcones XXII. The synthetic sequence for the preparation of compounds XIV as well as their use in the preparation of the aryltetralones VI is outlined in Scheme 7.

Scheme 7

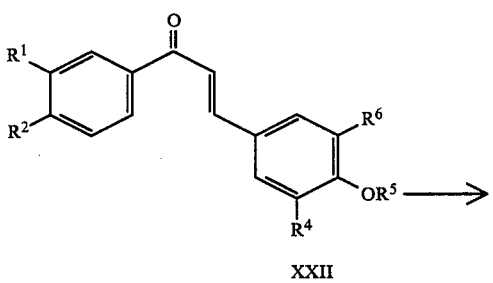

XXII

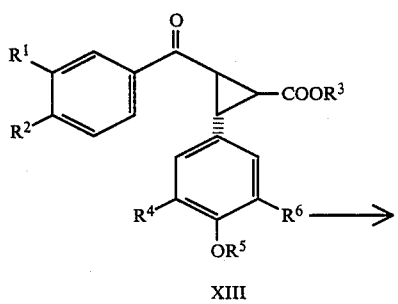

XIII

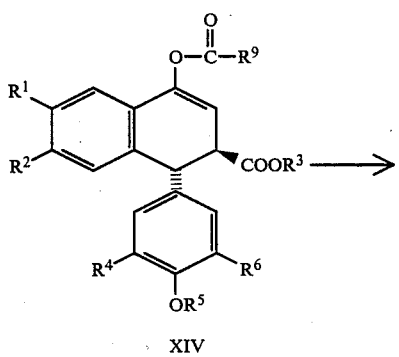

XIV

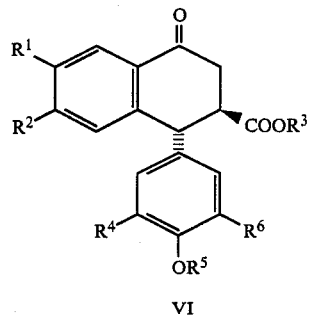

VI

The starting materials of the Formula XXII are readily prepared from known ketones and aryl aldehydes by the general procedures described by S. Wattanasin and W. S. Murphy in *Synthesis*, 647–650 (1980).

The cyclopropanation of the chalcones of Formula XXII to give the cyclopropyl ketones XIII may advantageously be carried out with well-known cyclopropanating agents, e.g. ethoxycarbonyl dimethylsulphonium methylide by the general procedure described by W. S. Murphy and S. Wattanasin in *J. C. S. Perkin I*, 271–276 (1982). The method of Murphy and Wattanasin, however, results in the formation of about a 1:1 mixture of α-COOR$^3$ and β-COOR$^3$ epimers of compounds of Formula XIII. It was also suggested by Murphy et al. that the α-isomer is the more important isomer for the subsequent cyclization reaction since the β-isomer epimerizes to the α-isomer under Lewis acid conditions within 10 minutes.

We have now found that the α-COOR$^3$ isomer of the cyclopropyl ketone XIIIa is formed exclusively in 96% yield when the cyclopropanation reaction is conducted in dimethylsulfoxide with the corresponding chalcone XXIIa wherein $R^1$ and $R^2$, taken together, is methylenedioxy; $R^4$ and $R^6$ is methoxy; $R^5$ is methyl and $R^3$ is ethyl.

The direct conversion by Lewis acid-catalyzed reactions of some of the cyclopropyl ketones of Formula XIII to the transaryltetralones of Formula VI is well-documented by W. S. Murphy and S. Wattanasin in *J. C. S. Perkin I*, 271–276 (1982) and references therein. Murphy et al. describe the successful cyclization of compound XIIIa wherein $R^1$ and $R^2$, taken together, is methylenedioxy; $R^4$ and $R^6$ are methoxy; $R^5$ is methyl and $R^3$ is ethyl to the corresponding important Gensler ketone VIb. The cyclization is characterized by the dramatic effect of the use of nitromethane as the solvent and the unsuccessful attempts to achieve this rearrangement in benzene and methylene chloride under a variety of conditions [W. S. Murphy and S. Wattanasin, *J. C. S. Chem. Comm.*, 262–263 (1980)]. However, the rearrangement of compound XIIIa to the aryltetralone VIb by the method of Murphy et al. proceeded rather slowly and yielded mixture of products. The best procedure utilizing BF$_3$·Et$_2$O in nitromethane for 15 days afforded a mixture of products and, at most, produced a 57% yield of compound VIb after preparative thin-layer chromatography as illustrated in Scheme 8.

Scheme 8

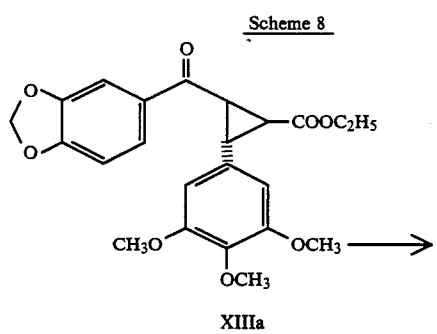

XIIIa

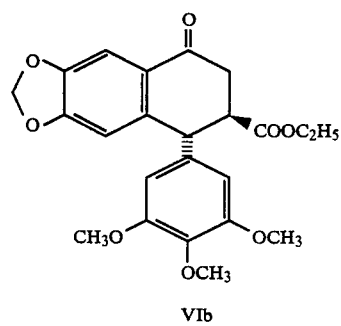

VIb

It is the purpose of the present embodiment of the invention to describe a new and significant improvement in the preparation of the aryltetralones VI via the novel enol compounds XIV.

A compound of Formula XIII is treated at about room temperature with an amount of about 0.5 equivalent of a Lewis acid, for example, SnCl$_4$, BF$_3$·Et$_2$O, ZnCl$_2$ or the like and at least 1 equivalent of an acid anhydride, for example, acetic anhydride or trifluoroacetic anhydride in an inert organic solvent such as nitromethane, methylene chloride, benzene, tetrahydrofuran, ethyl acetate, toluene, chloroform, dioxane, etc., to produce the enol compound of the Formula XIV. The solvent to be employed in the present embodiment is not critical. It is preferred to utilize 1 equivalent of a Lewis acid and 1 equivalent or, more preferably, 2 equivalents of an acid anhydride of the formula

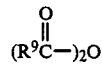

$(R^9C-)_2O$ wherein $R^9$ is as defined above. When the Lewis acid BF$_3$·Et$_2$O is utilized, it is advantageous to terminate and work up the reaction in about 5 minutes. However, if a weaker Lewis acid such as ZnCl$_2$ is utilized in the reaction, then it is preferred to continue the reaction for 24 hours before isolation of the corresponding enol compound XIV.

When it is desired to produce the aryltetralones VI, the cyclization of the corresponding cyclopropylketones XIII is carried out under the same conditions as described above for the preparation of the enol compounds XIV except that the reaction is allowed to proceed until the conversion to the aryltetralones VI is complete. Additionally, it was found that the cyclization reaction may be conducted with a catalytic amount of about 0.1 equivalent of an acid anhydride. It is preferred that the cyclization be carried out with 1 equivalent of an acid anhydride and most preferably with 2 equivalents in order to complete the reaction in about 1 to 2 hours and provide a purer product. In a procedure utilizing a weak Lewis acid such as ZnCl$_2$ and 2 equivalents of acid anhydride, it is preferred that the reaction be allowed to proceed for more than 24 hours. It is understood that if less than about 1 to 2 equivalents of an acid anhydride is used in the cyclization reaction, then longer reaction times may be necessary to complete the reaction.

In one of the specific examples exemplified in the present invention and illustrated in Scheme 9, Scheme 9

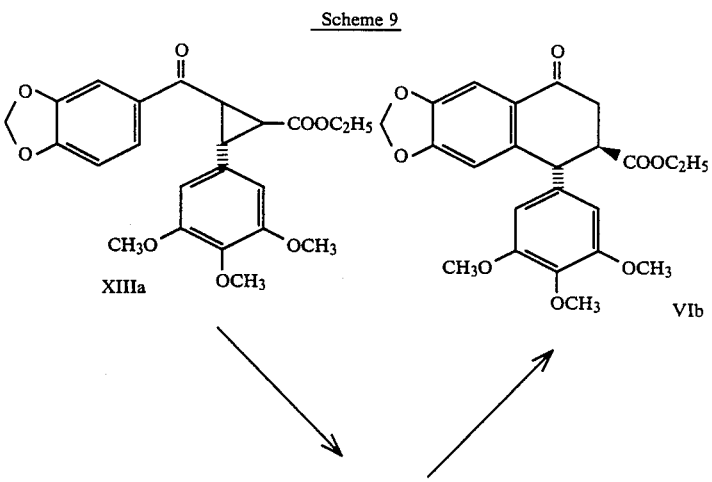

Scheme 9

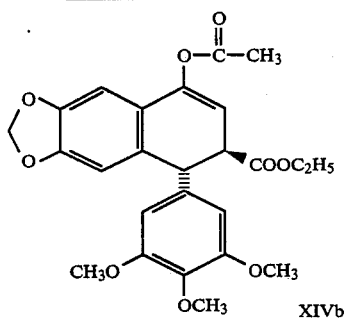

XIVb compound XIIIa was treated with 1 equivalent of BF$_3$·Et$_2$O and 2 equivalents of acetic anhydride to produce, in about 1 hour via the enol intermediate XIVb, a 96% yield of the aryltetralone VIb. In another example, Compound XIIIa was treated with 1 equivalent of ZnCl$_2$ and 2 equivalents of acetic anhydride to produce, in about 24 hours, a greater than 90% yield of the enol compound XIVb. The above examples, as well as other examples utilizing an acid anhydride, clearly and dramatically illustrate the general applicability and advantages of the present invention.

According to the present invention, there is also provided a process for preparing a compound of the formula

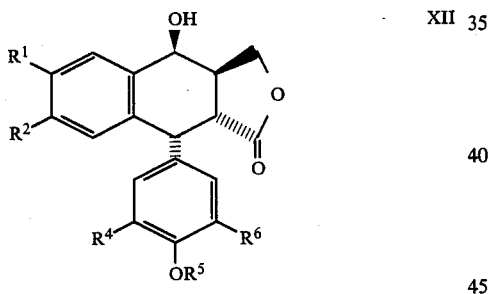

XII wherein R$^1$ and R$^2$ each are independently hydrogen or (lower)alkoxy, or R$^1$ and R$^2$, taken together, is methylenedioxy; R$^4$ and R$^6$ each are independently hydrogen or (lower)alkoxy; and R$^5$ is hydrogen or a phenol-protecting group, or a pharmaceutically acceptable addition salt thereof, comprising the steps of:

(a) reacting a cis-olefin of the formula

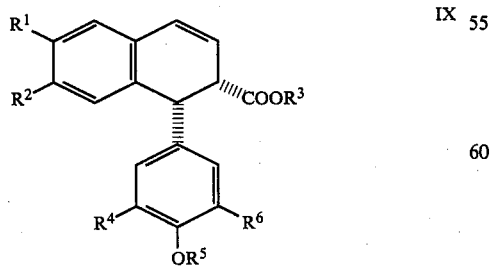

IX wherein R$^3$ is hydrogen or a carboxyl-protecting group; and R$^1$, R$^2$, R$^4$, R$^5$ and R$^6$ are as defined above, with a nitrile oxide of the formula

XX wherein R$^7$ is hydrogen, halogen, (lower)alkoxycarbonyl, carboxyl, cyano, trimethylsilyl, phenylsulfonyl or phenoxycarbonyl in which the phenyl ring or R$^7$ may contain one or two substituents independently selected from (lower)alkyl, halogen, (lower)alkoxy and trifluoromethyl, in an inert solvent, to produce an isoxazole of the formula

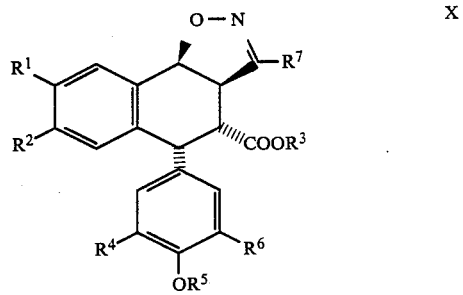

X wherein R$^1$, R$^2$, R$^3$, R$^4$, R$^5$, R$^6$ and R$^7$ are as defined above;

(b) cleaving the isoxazole ring of Formula X to produce a compound of the formula

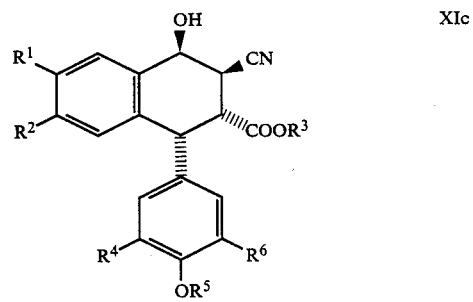

XIc wherein R$^1$, R$^2$, R$^3$, R$^4$, R$^5$ and R$^6$ are as defined above;

(c) selectively reducing the nitrile of Formula XIc to produce a compound of the formula

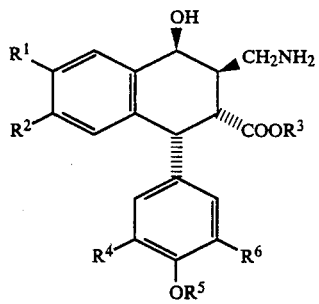

wherein $R^1$, $R^2$, $R^3$, $R^4$, $R^5$ and $R^6$ are as defined above, or a salt thereof; and, if $R^3$ is a carboxyl-protecting group, removing said carboxyl-protecting group to produce a compound of the Formula XId wherein $R^3$ is hydrogen; and (d) cyclizing the compound of Formula XId by diazotization of the amino radical followed by lactonization to produce a compound of the formula

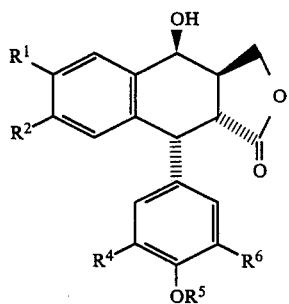

wherein $R^1$, $R^2$, $R^4$, $R^5$ and $R^6$ are as defined above.

A preferred embodiment of the present invention is the process of preparing an epipodophyllotoxin compound of the formula

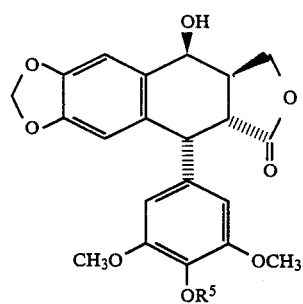

wherein $R^5$ is hydrogen or a phenol-protecting group, comprising the steps of:

(a) reacting a cis-olefin of the formula

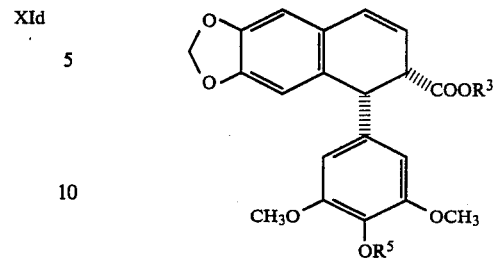

wherein $R^3$ is hydrogen or a carboxyl-protecting group and $R^5$ is hydrogen or a phenol-protecting group, with a nitrile oxide of the formula

wherein $R^7$ is hydrogen, halogen, (lower)alkoxycarbonyl, carboxyl, cyano, trimethylsilyl, phenylsulfonyl or phenoxycarbonyl in which the phenyl ring of $R^7$ may contain one or two substituents independently selected from (lower)alkyl, halogen, (lower)alkoxy and trifluoromethyl, in an inert solvent, to produce an isoxazole of the formula

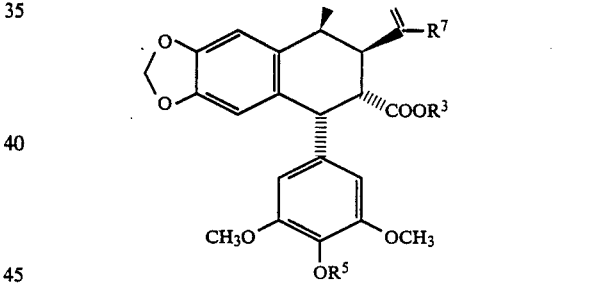

wherein $R^3$, $R^5$ and $R^7$ are as defined above;

(b) cleaving the isoxazole ring of Formula Xa to produce a compound of the formula

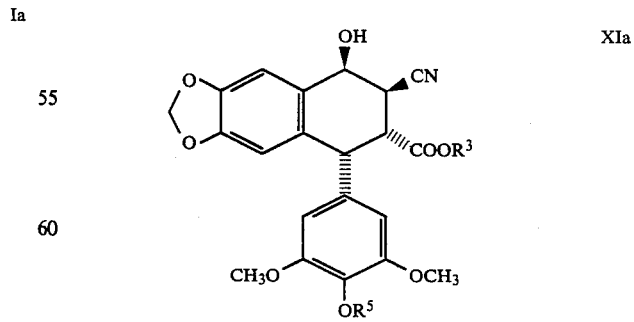

wherein $R^3$ and $R^5$ are as defined above;

(c) selectively reducing the nitrile of Formula XIa to produce a compound of the formula

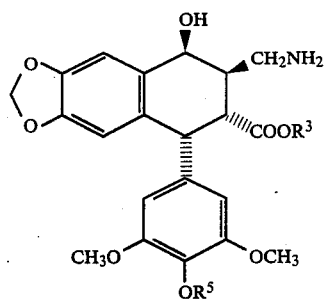

XIb wherein $R^3$ and $R^5$ are as defined above or a salt thereof; and, if $R^3$ is a carboxyl-protecting group, removing said carboxyl-protecting group to produce a compound of the Formula XIb wherein $R^3$ is hydrogen; and (d) cyclizing the compound of Formula XIb by diazotization of the amino radical followed by lactonization to produce an epipodophyllotoxin compound of the formula

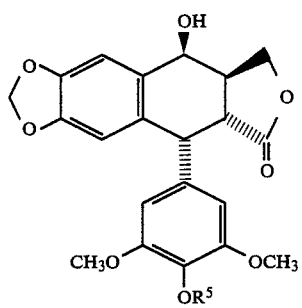

Ia wherein $R^5$ is as defined above.

Another embodiment of the present invention is the process for preparing a cis-olefin of the formula

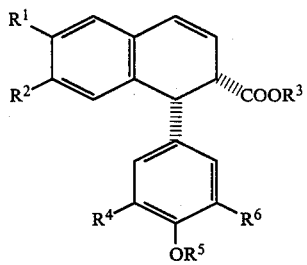

IX wherein $R^1$ and $R^2$ each are independently hydrogen or (lower)alkoxy, or $R^1$ and $R^2$, taken together, is methylenedioxy; $R^3$ is hydrogen or a carboxyl-protecting group; $R^4$ and $R^6$ each are independently hydrogen or (lower)alkoxy; and $R^5$ is hydrogen or a phenol-protecting group, comprising the steps of:

(a) dehydrating an alcohol of the formula

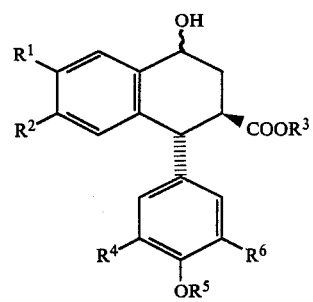

VII wherein $R^3$ is a carboxyl-protecting group; $R^5$ is a phenol-protecting group; and $R^1$, $R^2$, $R^4$ and $R^6$ are as defined above, in the presence of an acid to produce a trans-olefin of the formula

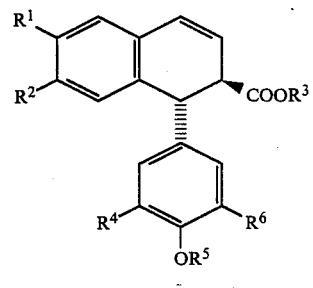

VIII wherein $R^1$, $R^2$, $R^3$, $R^4$, $R^5$ and $R^6$ are as defined above; and (b) epimerizing the trans-olefin of the Formula VIII by treatment with a strong base at low temperatures in an inert organic solvent followed by quenching with acid to produce a cis-olefin of the formula

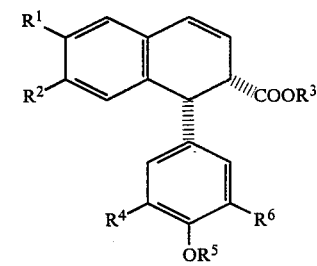

IX wherein $R^1$, $R^2$, $R^3$, $R^4$, $R^5$ and $R^6$ are as defined above, and optionally and selectively deblocking to produce a compound of Formula IX wherein $R^3$ is hydrogen and $R^5$ is a phenol-protecting group or $R^5$ is hydrogen and $R^3$ is a carboxyl-protecting group.

Another preferred embodiment of the present invention is the stereospecific process of preparing an isoxazole compound of the formula

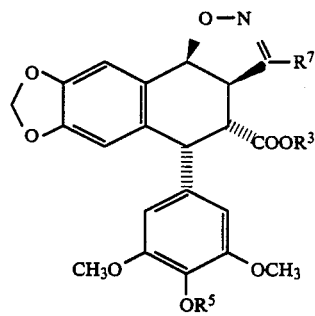

Xa wherein $R^3$ is hydrogen or a carboxyl-protecting group; $R^5$ is hydrogen or a phenol-protecting group and $R^7$ is hydrogen, halogen, (lower)alkoxycarbonyl, carboxyl, cyano, trimethylsilyl, phenylsulfonyl or phenoxycarbonyl in which the phenyl ring of $R^7$ may contain one or two substituents independently selected from (lower)alkyl, halogen, (lower)alkoxy and trifluoromethyl, comprising the step of reacting a cis-olefin of the formula

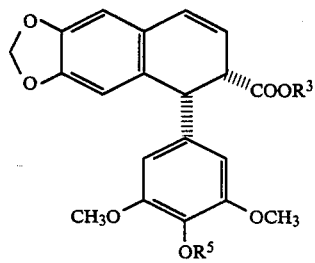

IXa wherein $R^3$ and $R^5$ are as defined above with a nitrile oxide of the formula

XX wherein $R^7$ is as defined above in an inert aqueous or organic, or mixed aqueous-organic solvent at about $-20°$ C. to refluxing temperature of the solvent to stereoselectively produce said isoxazole compound of the Formula Xa and optionally and selectively deblocking said compound of Formula Xa wherein $R^3$ is a carboxyl-protecting group to produce a compound of the formula

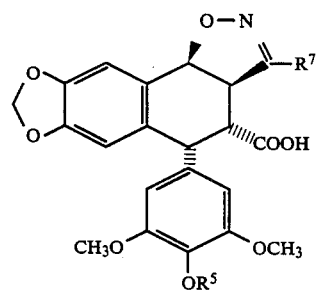

Xb wherein $R^5$ and $R^7$ are as defined above.

Still another preferred embodiment of the present invention is the process of preparing an epipodophyllotoxin compound of the formula

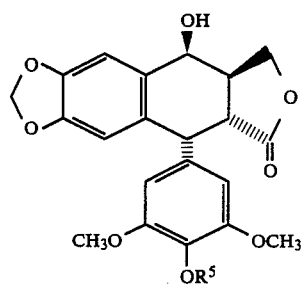

Ia wherein $R^5$ is hydrogen or a phenol-protecting group, comprising the steps of:

(a) cleaving the isoxazole ring of the formula

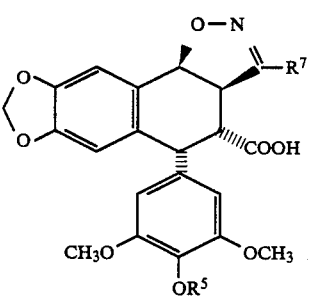

Xb wherein $R^5$ is hydrogen or a phenol-protecting group and $R^7$ is chlorine or bromine, to produce a nitrile of the formula

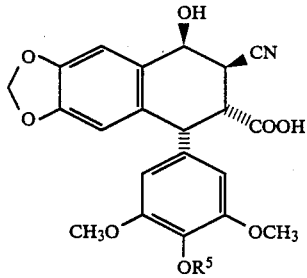

XIe wherein $R^5$ is hydrogen or a phenol-protecting group;

(b) selectively reducing the nitrile of Formula XIe to produce a compound of the formula

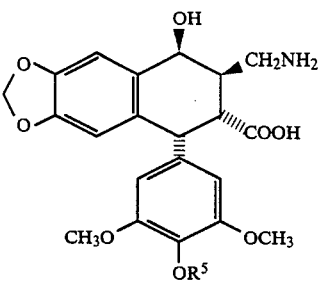

XIf wherein $R^5$ is hydrogen or a phenol-protecting group; and (c) cyclizing the compound of Formula XIf by diazotization of the amino radical followed by lactonization to produce an epipodophyllotoxin compound of the formula

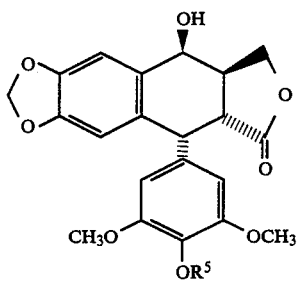

Ia

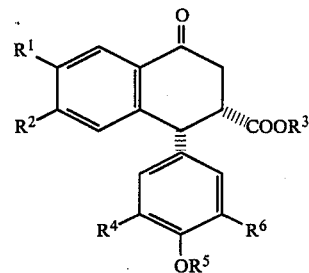

XVI wherein $R^5$ is hydrogen or a phenol-protecting group.

A variation of the above-described process for preparing compounds of the Formula XII involves the selective reduction of the trans-aryltetralone of Formula VI under hydrolyzing conditions or hydrolysis of the carboxylic ester of the trans-aryltetralone of Formula VI followed by selective reduction of the resultant acid VIa to produce a compound of Formula VIIa. Compound VIIa is then treated under dehydrating conditions in the presence of an acid to produce a trans-lactone of the formula

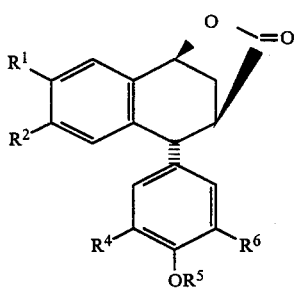

XV wherein $R^1$, $R^2$, $R^4$, $R^5$ and $R^6$ are as defined above. Compound XV is dehydrated in the presence of an acid and an alcohol $R^3$OH to produce a trans-olefin of the Formula VIII wherein $R^3$ is a carboxyl-protecting group. The trans-olefin VIII is then epimerized by enolate quenching to produce a cis-olefin of Formula IX. Compound IX is then reacted with a nitrile oxide of the Formula XX and the isoxazole of Formula X which is thereby produced is sequentially cleaved to a nitrile of Formula XIa and reduced to an amine of Formula XIb, and then diazotized according to the process described above to produce the desired compound of Formula XII.

A further variation of the above-described process for preparing the epipodophyllotoxin and epipodophyllotoxin related compounds of Formula XII involves epimerizing the trans-aryltetralone of Formula VI by enolate quenching to produce a cis-aryltetralone of the formula wherein $R^1$, $R^2$, $R^3$, $R^4$, $R^5$ and $R^6$ are as defined above. Compound XVI is then selectively reduced to produce a compound of the formula

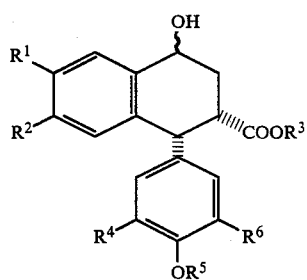

XVII wherein $R^1$, $R^2$, $R^3$, $R^4$, $R^5$ and $R^6$ are as defined above. Compound XVII is then dehydrated in the presence of an acid with removal of the water which is formed to produce a cis-olefin of the formula

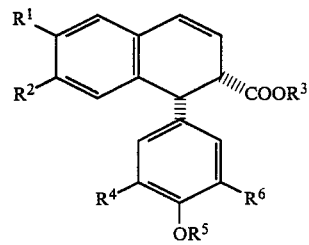

IX wherein $R^1$, $R^2$, $R^3$, $R^4$, $R^5$ and $R^6$ are as defined above. The cis-olefin of the Formula IX is then reacted with a nitrile oxide of the Formula XX, and the isoxazole of Formula X which is thereby produced is sequentially cleaved to a nitrile of the Formula XIa and reduced to an amine of the Formula XIb, and then diazotization according to the process described above to produce the desired compound of Formula XII.

A still further variation of the above-described process for preparing compounds of the Formula XII involves epimerizing the trans-aryltetralone of Formula VI by enolate quenching to produce a cis-aryltetralone of the formula

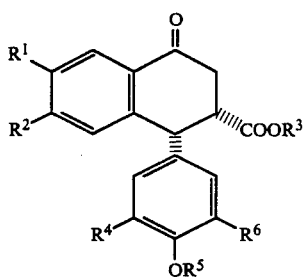

XVI wherein $R^1$, $R^2$, $R^3$, $R^4$, $R^5$ and $R^6$ are as defined above. Compound XVI is then selectively reduced under hydrolyzing conditions or hydrolyzed followed by selective reduction to produce a compound of the formula

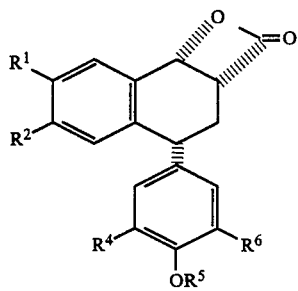

XVIII wherein $R^1$, $R^2$, $R^4$, $R^5$ and $R^6$ are as defined above. Compound XVIII is dehydrated in the presence of an acid and an alcohol $R^3OH$ to produce a cis-olefin of the formula

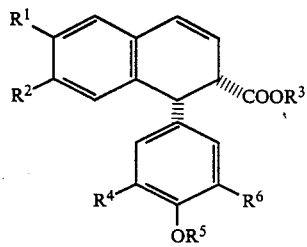

IX wherein $R^1$, $R^2$, $R^3$, $R^4$, $R^5$ and $R^6$ are as defined above. The cis-olefin of Formula IX is then reacted with a nitrile oxide of the Formula XX, and the isoxazole of the Formula X which is thereby produced is sequentially cleaved to a nitrile of the Formula XIa and reduced to an amine of the Formula XIb, and then diazotization according to the process described above to produce the desired compound of Formula XII.

In another aspect of the present invention, there is provided a process for preparing a compound of the formula

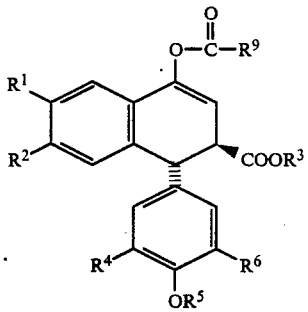

XIV wherein $R^1$ and $R^2$ each are independently hydrogen or (lower)alkoxy, or $R^1$ and $R^2$, taken together, is methylenedioxy; $R^3$ is hydrogen or a carboxyl-protecting group; $R^4$ and $R^6$ each are independently hydrogen or (lower)alkoxy; and $R^5$ is hydrogen or a phenol-protecting group, comprising the step of cyclizing a cyclopropyl compound of the formula

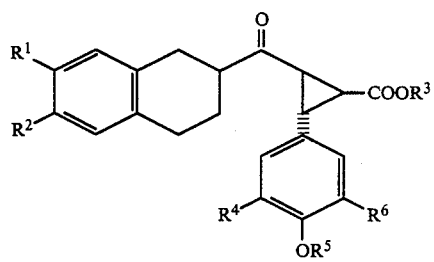

XIII wherein $R^1$, $R^2$, $R^3$, $R^4$, $R^5$ and $R^6$ are as defined above by treatment with at least 0.5 equivalent of a Lewis acid and at least one equivalent of an acid anhydride of the formula

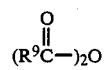

$(R^9C-)_2O$ wherein $R^9$ is phenyl or (lower)alkyl optionally substituted by one or more halogen atoms selected from fluorine, chlorine and bromine in an inert solvent until substantially the compound of the formula

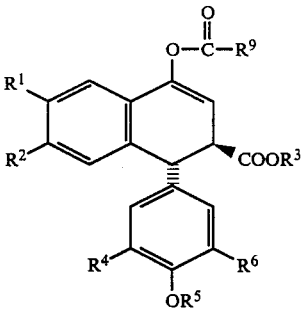

XIV is produced wherein $R^1$, $R^2$, $R^3$, $R^4$, $R^5$, $R^6$ and $R^9$ are as defined above.

In still another aspect of the present invention, there is provided a process for preparing a compound of the formula

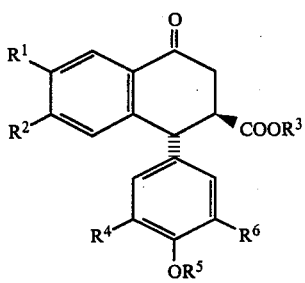

VI

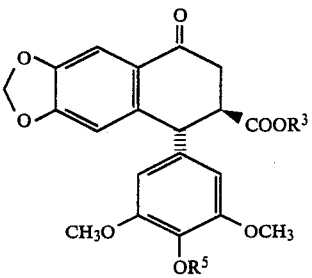

VIc wherein $R^1$ and $R^2$ each are independently hydrogen or (lower)alkoxy, or $R^1$ and $R^2$, taken together, is methylenedioxy; $R^3$ is hydrogen or a carboxyl-protecting group; $R^4$ and $R^6$ each are independently hydrogen or (lower)alkoxy; and $R^5$ is hydrogen or a phenol-protecting group, comprising the step of cyclizing a cyclopropyl compound of the formula

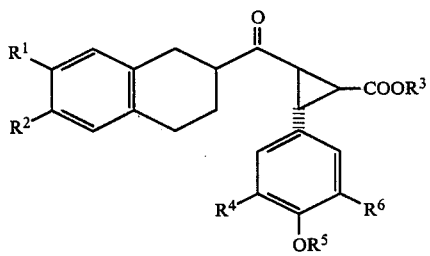

XIII wherein $R^1$, $R^2$, $R^3$, $R^4$, $R^5$ and $R^6$ are as defined above by treatment with at least 0.5 equivalent of a Lewis acid and at least a catalytic amount of an acid anhydride of the formula

wherein $R^9$ is phenyl or (lower)alkyl optionally substituted by one or more halogen atoms selected from fluorine, chlorine and bromine in an inert organic solvent until substantially the trans-aryltetralone of the formula

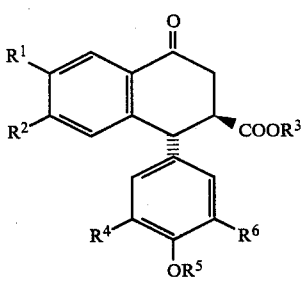

VI is produced wherein $R^1$, $R^2$, $R^3$, $R^4$, $R^5$ and $R^6$ are as defined above.

A preferred embodiment of the present invention is the process of preparing a trans-aryltetralone of the formula wherein $R^3$ is hydrogen or a carboxyl-protecting group and $R^5$ is hydrogen or a phenol-protecting group, comprising the step of cyclizing a cyclopropyl compound of the formula

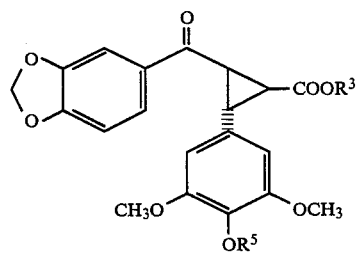

XIIIb wherein $R^3$ is a carboxyl-protecting group and $R^5$ is a phenol-protecting group by treatment with about one equivalent of a Lewis acid and about one to two equivalents of an acid anhydride of the formula

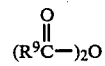

wherein $R^9$ is (lower) alkyl optionally substituted by one or more halogen atoms selected from fluorine, chlorine and bromine in an inert organic solvent until substantially the trans-aryltetralone of formula

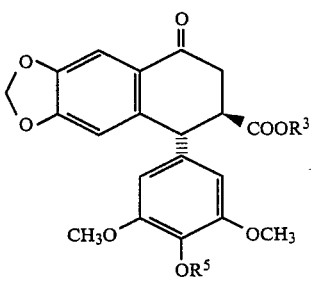

VIc is produced wherein $R^3$ and $R^5$ are as defined above, and optionally and selectively deblocking to produce a compound of Formula VIc wherein $R^3$ is hydrogen and $R^5$ is a phenol-protecting group or $R^5$ is hydrogen and $R^3$ is a carboxyl-protecting group.

DESCRIPTION OF SPECIFIC EMBODIMENTS

In the following examples, all temperatures are given in degrees Centigrade. Melting points were recorded on a Thomas-Hoover capillary melting point apparatus and are uncorrected. $^1$H NMR spectra were recorded on a Bruker WM 360 spectrometer in CDCl$_3$. Chemical shifts are reported in δ units and coupling constants in Hertz. Splitting patterns are designated as follows: s, singlet; d, doublet; t, triplet; q, quartet; m, multiplet; bp, broad peak; and dd, doublet of doublet. Infrared spectra were determined on a Beckman Model 4240 spectrophotometer and are reported in reciprocal centimeters. Thin-layer chromatography (TLC) was carried out on precoated silica gel plates (60F-254) using UV light and/or iodine vapors as visualizing agents. Flash chromatography was run with Woelm silica gel (32–63 μm) and the indicated solvents. All evaporations of solvents were performed under reduced pressure. As used herein, the term Skellysolve B is a petroleum solvent fraction having a bp range of 60°–68° C. consisting essentially of n-hexane, and the term "ether" is diethyl ether unless otherwise indicated.

EXAMPLE 1

Ethyl 2-(3,4-methylenedioxybenzoyl)-3-(3,4,5-trimethoxyphenyl)cyclopropane carboxylate (XIIIa)

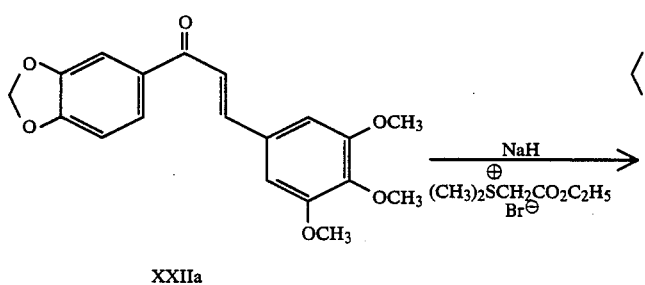

XXIIa

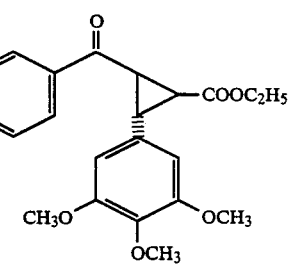

XIIIa

In a three-neck one-liter round-bottom flask, equipped with a magnetic stirrer, dropping funnel, nitrogen inlet and a septum was placed sodium hydride (8.2 g, 0.17 moles, 50% dispersion). The dispersion was washed with petroleum ether (2×100 ml) and dried under nitrogen. Trimethylsulfoxonium iodide (37.7 g, 0.17 moles) was added, followed by a dropwise addition of dry dimethylsulfoxide (45 ml) via a syringe over a 30-minute period. The suspension was stirred at room temperature for 1.5 hours, and then a solution of carbethoxymethyl dimethylsulfonium bromide (41.2 g, 0.18 moles) in dimethylsulfoxide (60 ml) was added over a 10-minute period, under continuous stirring. The milky white suspension was further stirred at room temperature for 1.5 hours. A suspension of 3,4,5-trimethoxy-3',4'-methylenedioxy chalcone XXIIa (55.9 g, 0.16 moles) [prepared according to the procedure described by S. Wattanasin and W. S. Murphy, *Synthesis*, 647 (1980)] in dimethylsulfoxide (185 ml) was added in a steady stream over a 5-minute period, and then the reaction mixture was stirred at room temperature for 17 hours. The reaction mixture was poured into cold 0.1N HCl (700 ml), and the resulting gummy material was separated from the aqueous solution. The aqueous solution was extracted with ether (2×500 ml). The combined extract together with an additional amount of ether (500 ml) was employed to dissolve the gummy precipitate. The etheral solution was sequentially washed with aqueous NaHCO₃ solution (500 ml, 5%) and water, dried (Na₂SO₄ and MgSO₄) and concentrated to yield the α-isomer of the title compound (68.0 g) as a light-yellow glass. The ¹H NMR spectral data of this material was identical to the α-isomer reported by W. S. Murphy and S. Wattanasin, *J. C. S. Perkin I*, 271 (1982).

In another experiment, the trimethylsulfoxonium iodide which was utilized in the above procedure was omitted from the reaction to also afford, in high yield, the α-isomer of the title compound. Thus, to a solution of sodium hydride (0.67 g, 1.4 mM, 50% dispersion) in 10 ml of dry dimethylsulfoxide was added carbethoxymethyl dimethylsulfonium bromide (2.98 g, 1.2 mM) followed by an additional 19 ml of dimethylsulfoxide. After approximately 75 minutes, a solution of the chalcone XXIIa (3.42 g, 1.0 mM) in 21 ml of tetrahydrofuran and 4 ml of dimethylsulfoxide was slowly added over a 35-minute period. The reaction mixture was worked up as in the above procedure to give the α-isomer of the title compound in 96% yield.

EXAMPLE 2

Trans-ethyl 1,2,3,4-tetrahydro-6,7-methylenedioxy-4-oxo-1-(3,4,5-trimethoxyphenyl)naphthalene-2-carboxylate (VIb)

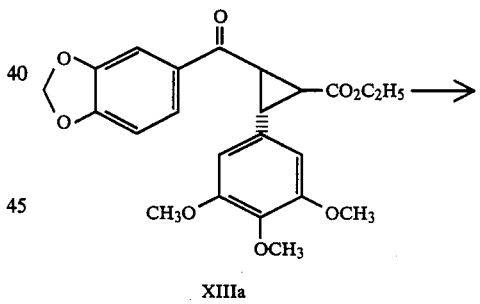

XIIIa

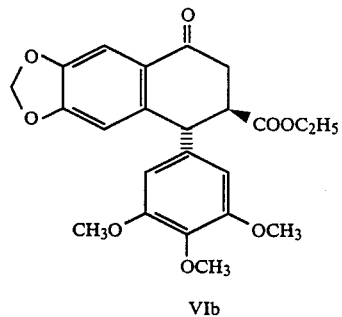

VIb

To a solution of cyclopropylketone XIIIa (0.8 g, 1.8 mM) in methylene chloride (40 ml) was added BF₃·Et₂O (0.24 ml, 19 mM) followed by acetic anhydride (0.36 ml, 3.8 mM). The solution was stirred at room temperature for 2.5 hours and then diluted with 0.2N sodium hydroxide solution (50 ml) and methylene chloride (50 ml). The organic layer was separated, washed (H₂O), dried (MgSO₄) and concentrated to an oily solid (0.72 g). Recrystallization from absolute ethanol with charcoal treatment afforded the title compound as a white crystalline solid (0.46 g); m.p. 157°-159° C. The $^1$H NMR spectral data was in agreement with that reported by W. S. Murphy and S. Wattanasin, *J. C. S. Perkin I*, 271 (1982).

EXAMPLE 3

Trans-ethyl 1,2,3,4-tetrahydro-6,7-methylenedioxy-4-oxo-1-(3,4,5-trimethoxyphenyl)naphthalene-2-carboxylate (VIb)

The procedure of Example 2 was repeated with 50 mg (0.12 mM) of cyclopropylketone XIIIa except that the methylene chloride utilized therein was replaced with nitromethane, and there was thereby produced 45 mg of the title compound; TLC [silica gel/ether:Skellysolve B (3:2)] gave $R_f$=0.26. The $^1$H NMR spectral data was identical to the product produced in Example 2.

EXAMPLE 4

Trans-ethyl 1,2,3,4-tetrahydro-6,7-methylenedioxy-4-oxo-1-(3,4,5-trimethoxyphenyl)naphthalene-2-carboxylate (VIb)

(a) The procedure of Example 2 was repeated in methylene chloride with 50 mg (0.12 mM) of cyclopropylketone XIIIa except that the BF₃·Et₂O utilized therein was replaced with SnCl₄, and there was thereby produced about 90% yield of the title compound.

(b) The above procedure (a) was repeated except that the methylene chloride utilized therein was replaced with nitromethane, and there was thereby produced about 90% yield of the title compound.

(c) The above procedure (a) was again repeated except that the methylene chloride utilized therein was replaced with benzene, and there was thereby produced the title compound.

The TLC [silica/ether:Skellysolve B (3:2)] of each of the above three products gave $R_f$=0.26, and the $^1$H NMR spectral data were identical to the product produced in Example 2.

EXAMPLE 5

Trans-ethyl 1,2,3,4-tetrahydro-6,7-methylenedioxy-4-oxo-1-(3,4,5-trimethoxyphenyl)naphthalene-2-carboxylate (VIb)

The procedure of Example 3 was repeated with 428 mg (1.0 mM) of cyclopropylketone XIIIa and 204 mg (2.0 mM) of acetic anhydride in 5 ml of nitromethane, except that the 1 equivalent of BF₃·Et₂O utilized therein was replaced with 0.5 equivalent of BF₃·Et₂O (71 mg, 0.5 mM), and there was thereby produced the title compound. The $^1$H NMR spectral data was identical to the product produced in Example 3.

EXAMPLE 6

Trans-ethyl 1,2,3,4-tetrahydro-6,7-methylenedioxy-4-oxo-1-(3,4,5-trimethoxyphenyl)naphthalene-2-carboxylate (VIb)

To a solution of cyclopropylketone XIIIa (428 mg, 1.0 mM) in 5 ml of nitromethane was added a catalytic amount of acetic anhydride (10.2 mg, 0.1 mM) followed by BF₃·Et₂O (142 mg, 1.0 mM). The reaction was stirred at room temperature and followed by high pressure liquid chromatography. After about 100 hours, the reaction mixture was treated with 10 ml of 0.2N NaOH and diluted with 5 ml of methylene chloride. The organic phase was separated, dried and evaporated under reduced pressure to give the title compound. The $^1$H NMR spectrum was identical to the product produced in Example 2 except for the presence of some impurities.

EXAMPLE 7

Trans-ethyl 1,2-dihydro-6,7-methylenedioxy-4-acetoxy-1-(3,4,5-trimethoxyphenyl)naphthalene-2-carboxylate (XIVb)

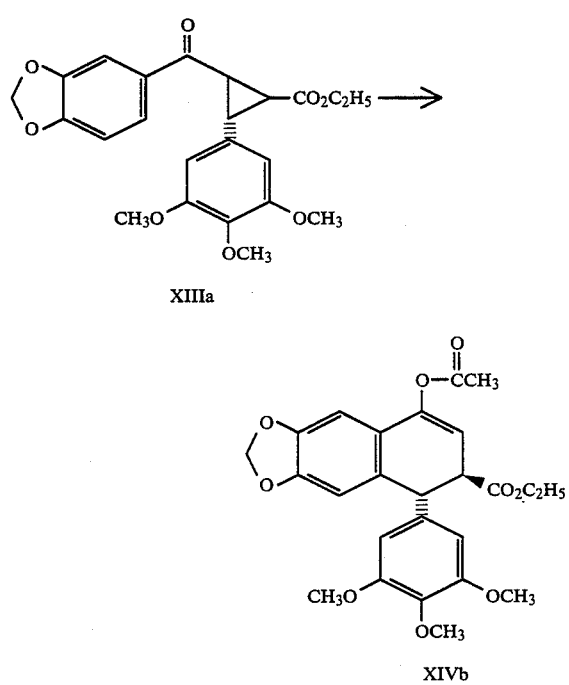

XIIIa

XIVb

To a solution of cyclopropylketone XIIIa (1.40 g, 3.24 mM) in methylene chloride (50 ml) was added acetic anhydride (0.61 ml, 6.47 mM) followed by BF₃·Et₂O (0.40 ml, 3.25 mM). The solution was stirred for 5 minutes and then treated with 0.5N sodium hydroxide solution (35 ml). The organic layer was separated, washed (H₂O), dried (MgSO₄) and concentrated to a syrup (1.53 g). Thin-layer chromatography [ethyl acetate:methylene chloride (5:95)] revealed two major spots at $R_f$'s=0.47 and 0.27 ($R_f$ of starting material=0.36). Silica gel column chromatography, using 3% ethyl acetate in methylene chloride as eluting solvent, afforded the two compounds in analytical purity.

The faster component (0.52 g, $R_f$=0.47) was characterized as the title compound, m.p. 124°-129° C.

Anal. Calc'd for $C_{25}H_{26}O_9$: C, 63.82; H, 5.57

Found: C, 63.52; H, 5.74

$^1$H NMR (CDCl₃, δ): 1.18(t, 3H, 7.2 Hz), 2.31(s, 3H), 3.62(t, 1H, 5.5 Hz), 3.81(s, 9H), 4.10(q, 2H), 4.49(d, 1H, 5.5 Hz), 5.55(d, 1H, 5.7 Hz), 5.92(s, 2H), 6.52(s, 3H), 6.68(s, 1H).

The slower component (0.40 g, $R_f$=0.27) was identified as the tetralone VIb, which was identical to the compound obtained in Example 2.

EXAMPLE 8

Trans-ethyl 1,2-dihydro-6,7-methylenedioxy-4-acetoxy-1-(3,4,5-trimethoxyphenyl)naphthalene-2-carboxylate (XIVb)

The procedure of Example 7 was repeated except that the $BF_3 \cdot Et_2O$ utilized therein was replaced with $ZnCl_2$ and, after 24 hours at room temperature, the reaction gave >90% yield of the title compound; TLC [silica/ethyl acetate:methylene chloride (5:95)] gave $R_f=0.47$. The $^1H$ NMR spectral data was identical to the product produced in Example 7.

EXAMPLE 9

Cis-ethyl 1,2,3,4-tetrahydro-6,7-methylenedioxy-4-oxo-1-(3,4,5-trimethoxyphenyl)naphthalene-2-carboxylate (XVIb)

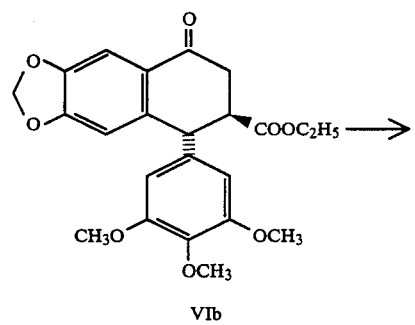

VIb

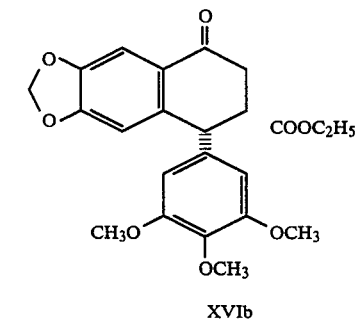

XVIb

To a solution of 1.7M n-BuLi in hexane (10.6 ml, 18.0 mM) in tetrahydrofuran (10 ml) at −78° C. and under nitrogen was added slowly diisopropylamine (2.52 ml, 18.0 mM). After stirring the solution for 20 minutes, a solution of trans-tetralone VIb (1.93 g, 4.51 mM) in tetrahydrofuran (40 ml) was added dropwise over a period of 30 minutes at −78° C. After the addition was complete, the orange mixture was slowly warmed to −40° C. over a 1-hour period and further stirred for 30 minutes. A solution of concentrated HCl (3.5 ml) in tetrahydrofuran (3.5 ml) was then added in one portion to yield a pale yellow solution. After warming to room temperature, the mixture was diluted with 50 ml of water and extracted with ethyl acetate. The combined organic extract was dried (MgSO4) and concentrated to give 2.1 g of product, which was crystallized from 95% ethanol. Recrystallization from absolute ethanol with slow cooling to room temperature yielded the title compound as a crystalline solid; m.p. 136.5°–137.5° C.

$^1H$ NMR (CDCl$_3$, δ): 1.24(t, 3H, 8 Hz), 2.88(m, 2H), 3.52(m, 1H), 3.76(s, 6H), 3.84(s, 3H), 4.16(q, 2H, 8 Hz), 4.72(d, 1H, 6 Hz), 6.10(s, 2H), 6.24(s, 2H), 6.68(s, 1H), 7.64(s, 1H).

EXAMPLE 10

Ethyl 1,2,3,4-tetrahydro-6,7-methylenedioxy-4-hydroxy-1-(3,4,5-trimethoxyphenyl)naphthalene-2-carboxylate (VIId)

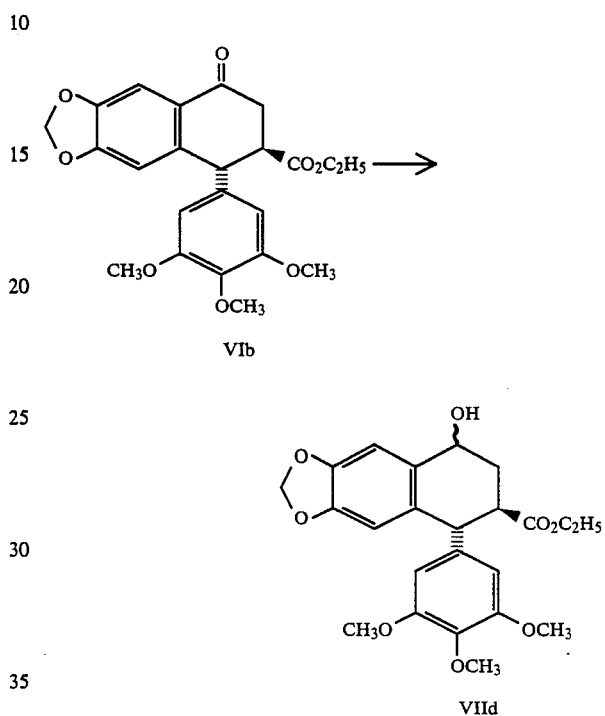

To a solution of tetralone VIb (6.25 g, 14.6 mM) in 95% ethanol (100 ml) and methylene chloride (50 ml) was added a cold solution of sodium borohydride (0.42 g, 11.1 mM) in water (5 ml). The solution was stirred at room temperature for 3 hours and at 40° C. for 30 minutes. The solution was diluted with water (50 ml) and concentrated to a solid residue at 35° C. The residue was partitioned between methylene chloride (100 ml) and water (100 ml). The aqueous layer was further extracted with methylene chloride (100 ml), and the combined organic extract was dried (MgSO4) and concentrated to a solid residue (5.95 g). Recrystallization from 95% ethanol afforded the title compound as a crystalline solid; m.p. 151°–152° C.

Anal. Calc'd for $C_{23}H_{26}O_8$: C, 64.18; H, 6.09

Found: C, 64.03; H, 6.02

$^1H$ NMR (CDCl$_3$, δ): 1.15(t, 3H, 7.2 Hz), 2.06(m, 1H), 2.35(m, 1H), 2.46(d, 1H, 8.6 Hz), 2.95(m, 1H), 3.78(s, 6H), 3.82(s, 3H), 4.06(q, 2H, 7.2 Hz), 4.31(d, 1H, 7.7 Hz), 4.83(m, 1H), 5.91(2H), 6.24(s, 2H), 7.07(s, 1H).

IR (KBr), $\nu$max, cm$^{-1}$: 3290, 1730, 1725, 1590, 1235, 1122.

EXAMPLE 11

Trans-ethyl 1,2-dihydro-6,7-methylenedioxy-1-(3,4,5-trimethoxyphenyl)naphthalene-2-carboxylate (VIIIb)

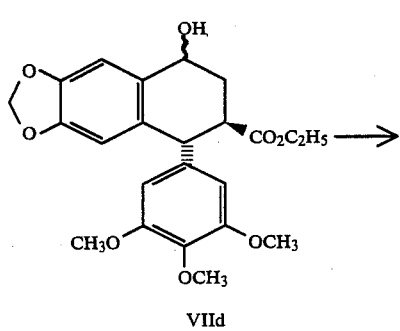

VIId

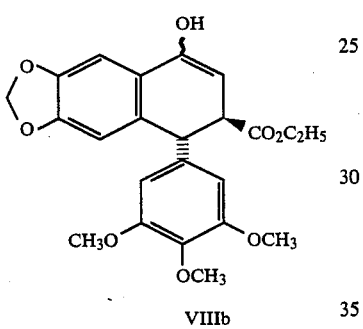

VIIIb

A suspension of alcohol VIId (0.43 g, 1.0 mM) in toluene (15 ml) containing p-toluenesulfonic acid monohydrate (4 mg) was heated to reflux with a Dean-Stark trap for 1 hour. Thin-layer chromatography [ethyl acetate:Skellysolve B (1:1)] revealed that all of the starting material ($R_f$=0.40) was converted to a new compound ($R_f$=0.69). The solution was cooled, washed with 5% aqueous sodium bicarbonate solution and water, followed by concentration under reduced pressure to an oil silica gel (20 g) using methylene chloride and 3% ethyl acetate in methylene chloride as eluting solvent to yield the title compound ($R_f$=0.69) as a white amorphous solid; m.p. 129.5°–130.5° C.

Anal. Calc'd for $C_{23}H_{24}O_7$: C, 66.98; H, 5.87

Found: C, 66.83; H, 5.87

$^1$H NMR (CDCl$_3$, δ): 1.14(t, 3H, 7.3 Hz), 3.58(m, 2H), 3.80(s, 6H), 3.83(s, 3H), 4.07(q, 2H, 7.3 Hz), 4.40(d, 1H, 9.4 Hz), 5.82(dd, 1H, 3.9 Hz, 9.6 Hz), 5.89(t, 2H), 6.39(s, 1H), 6.42(s, 2H), 6.49(dd, 1H, 2.0 Hz, 9.6 Hz), 6.63(s, 1H).

IR (KBr), νmax, cm$^{-1}$: 1726, 1580, 1240, 1125.

EXAMPLE 12

1,2,3,4-Tetrahydro-6,7-methylenedioxy-4-hydroxy-1-(3,4,5-trimethoxyphenyl)naphthalene-2-carboxylic acid (VIIb)

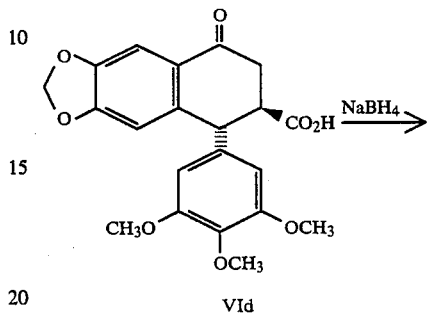

VId

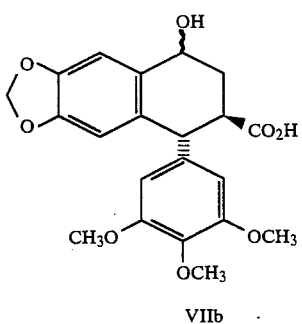

VIIb

The tetralone VIb prepared in Example 2 was hydrolyzed according to the procedure described by W. S. Murphy and S. Wattanasin, *J. C. S. Perkin I*, 271 (1982), and the resulting 1,2,3,4-tetrahydro-6,7-methylenedioxy-4-oxo-1-(3,4,5-trimethoxyphenyl)naphthalene-2-carboxylic acid (VId) was treated with sodium borohydride according to the general procedure described by W. J. Gensler et al., *J. Am. Chem. Soc.*, 82, 1714 (1960) to give the title compound as a crystalline solid; m.p. 191.5°–193° C. (reported m.p. 181.4°–182° C.).

EXAMPLE 13

Trans-1,2-dihydro-6,7-methylenedioxy-1-(3,4,5-trimethoxyphenyl)naphthalene-2-carboxylic acid (VIIIc)

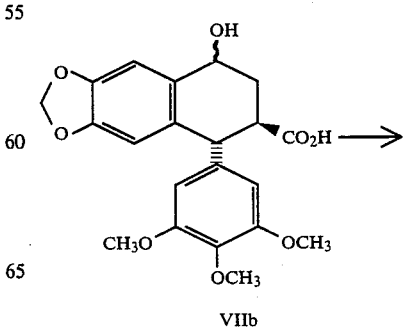

VIIb

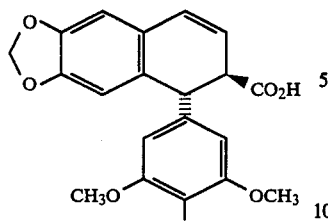

VIIIc

A suspension of alcohol VIIb (400 mg, 0.99 mM) in toluene (20 ml) containing p-toluenesulfonic acid monohydrate (10 mg) was refluxed for 2 hours using a Dean-Stark trap. The reaction solution was cooled, washed with water (15 ml), dried (MgSO$_4$) and concentrated to a white solid (364 mg). Recrystallization and charcoal treatment of solid from methanol afforded the title compound as a crystalline solid; m.p. 177°–180° C.

Anal. Calc'd for C$_{21}$H$_{20}$O$_7$: C, 65.62; H, 5.24
Found: C, 65.61; H, 5.26

$^1$H NMR (CDCl$_3$, δ): 3.60(m, 1H), 3.78(s, 6H), 3.82(s, 3H), 4.40(d, 1H, 7.8 Hz), 5.83(dd, 1H, 4.6 Hz, 9.6 Hz), 5.91(d, 2H), 6.39(s, 2H), 6.41(s, 1H), 6.53(dd, 1H, 1.8 Hz, 9.7 Hz), 6.64(s, 1H).

IR (KBr), νmax, cm$^{-1}$: 1745, 1710, 1590, 1510, 1485, 1250, 1130.

EXAMPLE 14

Trans-benzhydryl 1,2-dihydro-6,7-methylenedioxy-1-(3,4,5-trimethoxyphenyl)naphthalene-2-carboxylate (VIIIa)

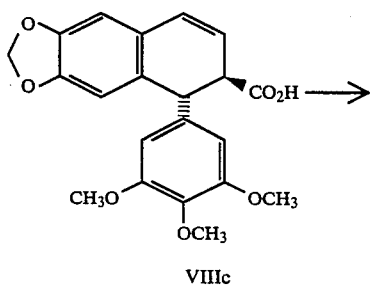

VIIIc

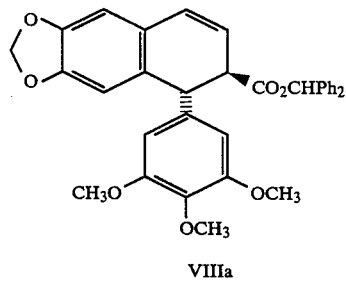

VIIIa

A solution of acid VIIIc (1.63 g, 4.24 mM), benzhydryl alcohol (0.79 g, 4.29 mM), p-toluenesulfonic acid monohydrate (37 mg) in toluene (100 ml) was refluxed for 2 hours using a Dean-Stark trap. The progress of the reaction was monitored by thin-layer chromatography (2% ethyl acetate in methylene chloride). The solution was cooled to room temperature and washed with 5% aqueous sodium bicarbonate solution (90 ml), water (50 ml), dried (MgSO$_4$) and concentrated to a brown oil (2.43 g), which was further purified by column chromatography (silica gel) to afford the title compound as a solid amorphous material; m.p. 149°–156° C.

Anal. Calc'd for C$_{34}$H$_{30}$O$_7$: C, 74.17; H, 5.49
Found: C, 74.13; H, 5.62

$^1$H NMR (CDCl$_3$, δ): 3.72(s, 6H), 3.73(m, 1H), 3.83(s, 3H), 4.41(d, 1H, 9.6 Hz), 5.84(dd, 1H, 4.2 Hz, 9.6 Hz), 5.89(t, 2H), 6.35(s, 1H), 6.38(s, 2H), 6.52(dd, 1H, 2.0 Hz, 9.6 Hz), 6.65(s, 1H), 6.77(s, 1H), 7.37–7.07(m, 10H).

EXAMPLE 15 dl-8,9-Dihydro-9-(3,4,5-trimethoxyphenyl)-5,8-methano-1,3-dioxolo(4,5-h)(2)benzoxepin-7(5H)-one(5β,8β,9α) (XVa)

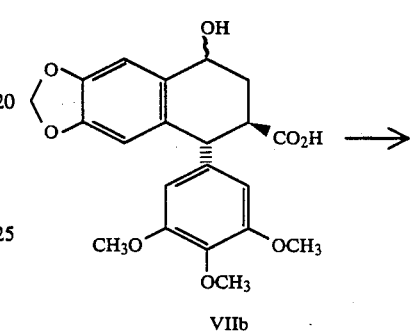

VIIb

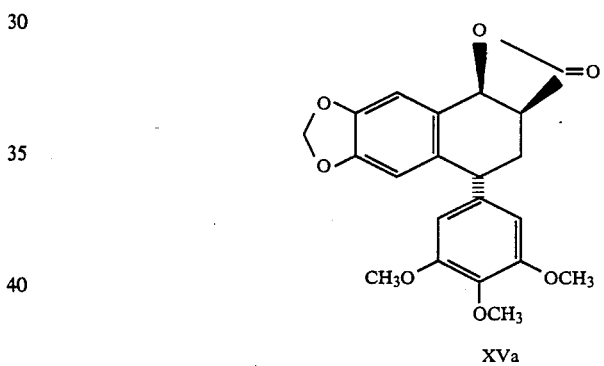

XVa

A suspension of alcohol VIIb (42.9 g, 0.107 mole) in 1 liter of toluene containing p-toluenesulfonic acid monohydrate (500 mg) was heated at reflux temperature for about 2.5 hours using a Dean-Stark trap. The mixture was then treated with 19.6 g (0.107 mole) of benzhydryl alcohol in an additional 100 ml of toluene and refluxed for 3 additional hours. The reaction mixture was washed with 5% aqueous Na$_2$CO$_3$ and a saturated NaCl solution, dried (MgSO$_4$) and concentrated to 49.0 g.

The residue was purified by column chromatography over silica gel (350 g) using methylene chloride to 5% ethyl acetate in methylene chloride as eluting solvent to yield the title compound. A sample was recrystallized from 95% ethanol with charcoal treatment to yield the title compound as a crystalline solid; m.p. 191.5°–193° C.

Anal. Cal'd for C$_{21}$H$_{20}$O$_7$: C, 65.79; H. 5.26
Found: C, 65.32; H. 5.30

$^1$H NMR (CDCl$_3$, δ): 2.43 (m, 2H), 2.98(d, 1H, 5.0 Hz), 3.78(s, 6H), 3.84(s, 3H), 4.40(bs, 1H), 5.25(d, 1H, 4.8 Hz), 5.97(m, 2H), 6.29(s, 2H), 6.49(s, 1H), 6.75(s, 1H).

In another experiment, the above procedure was repeated except that the benzhydryl alcohol utilized therein was omitted from the reaction, and there was thereby produced the desired lactone XVa.

EXAMPLE 16

Trans-benzhydryl 1,2-dihydro-6,7-methylenedioxy-1-(3,4,5-trimethoxyphenyl)naphthalene-2-carboxylate (VIIIa)

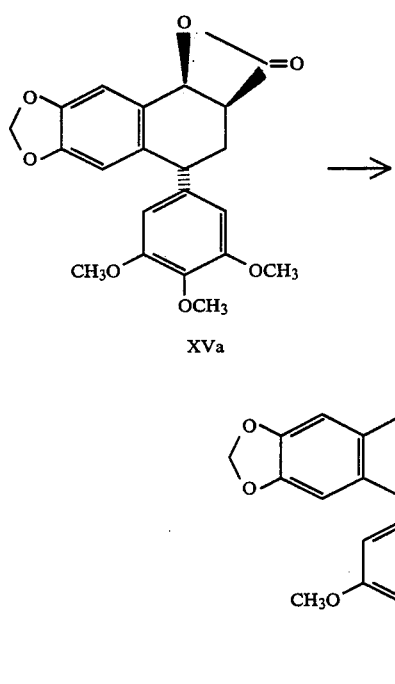

A mixture of the lactone XVa (3.9 g, 10.2 mM) and benzhydryl alcohol (1.87 g, 10.2 mM) in 100 ml of toluene containing p-toluenesulfonic acid monohydrate (200 mg) was heated at reflux temperature for about 2.5 hours using a Dean-Stark trap. After the theoretical amount of water was collected (0.2 ml), the reaction mixture was washed with a saturated $NaHCO_3$ solution and a saturated NaCl solution, dried ($MgSO_4$) and concentrated to an oil, which was further purified by eluting a methylene chloride solution of the oil through a pad of silica gel (15 g) with an additional amount of methylene chloride (75 ml). The filtrate was evaporated under reduced pressure to yield 4.06 g of product as an oil. A sample was further purified by column chromatography (alumina) using methylene chloride to 2% ethyl acetate in methylene chloride as eluant to yield the title compound as a solid amorphous material which was identical to the product produced in Example 14; m.p. 149°-156° C.

EXAMPLE 17

Cis-ethyl 1,2-dihydro-6,7-methylenedioxy-1-(3,4,5-trimethoxyphenyl)naphthalene-2-carboxylate (IXb)

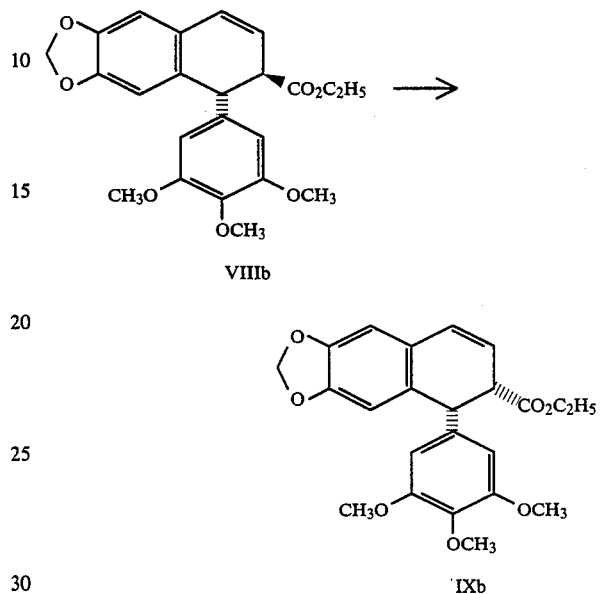

To a solution of 1.7M nBuLi in hexane (7.3 ml, 12.4 mM) in tetrahydrofuran (20 ml) at −78° C. and under nitrogen was added dropwise diisopropylamine (1.75 ml, 12.5 mM). After stirring for 5 minutes, a solution of trans-olefin VIIIb (2.06 g, 5.0 mM) in tetrahydrofuran (10 ml) was added dropwise over a twenty-minute period by a syringe. After the addition was complete, the reaction mixture was warmed to −40° C. over a 30-minute period and stirred at this temperature for 30 minutes. To this stirred solution was added concentrated HCl (2.2 ml) in cold tetrahydrofuran (2.5 ml). The dry-ice acetone bath was removed, and the reaction mixture was warmed to room temperature. Tetrahydrofuran was removed under reduced pressure, and the resulting residue was partitioned between water (100 ml) and methylene chloride (100 ml). The aqueous layer was further extracted with methylene chloride (50 ml), and the combined organic extract was washed with water (100 ml), dried ($MgSO_4$) and concentrated to an oil (2.1 g). This oil was further purified by silica gel column chromatography using 5% ethyl acetate in methylene chloride as eluting solvent to yield the title compound as an amorphous solid (1.74 g). Recrystallization from ethanol afforded an analytical sample; m.p. 112°-113° C.

Anal. Calc'd for $C_{23}H_{24}O_7$: C, 66.98; H, 5.87

Found: C, 66.87; H, 5.82

$^1$H NMR ($CDCl_3$, δ): 1.12(t, 3H, 7.2 Hz), 3.75(s, 6H), 3.76(s, 3H), 4.07–3.95(m, 3H), 4.30(d, 1H, 7.7 Hz), 6.11(m, 2H), 6.45(s, 2H), 6.50(dd, 1H, 3.0 Hz, 9.7 Hz), 6.61(s, 1H), 6.65(s, 1H).

IR (KBr), νmax, cm$^{-1}$: 1730, 1592, 1508, 1490, 1250, 1130.

EXAMPLE 18

Cis-benzhydryl 1,2-dihydro-6,7-methylenedioxy-1-(3,4,5-trimethoxyphenyl)naphthalene-2-carboxylate (IXc)

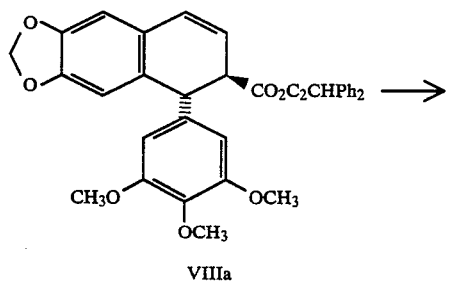

The procedure of Example 17 was repeated, except that the trans-olefin VIIIb utilized therein was replaced by the trans-olefin VIIIa, and there was thereby produced the title compound as a waxy solid.

Anal. Calc'd for $C_{34}H_{30}O_7$: C, 74.17; H, 5.49
Found: C, 74.17; H, 5.76

$^1$H NMR (CDCl$_3$, δ): 3.51(s, 6H), 3.73(s, 3H), 4.38(dt, 1H, 7.4Hz, 2.9 Hz), 4.38(d, 1H, 7.5 Hz), 5.91(2H), 6.19(dd, 1H, 2.7 Hz, 9.7 Hz), 6.40(s, 2H), 6.51(dd, 1H, 2.9 Hz, 9.8 Hz), 6.65(s, 2H), 6.75(s, 1H), 7.11–7.37(m, 10H).

EXAMPLE 19 dl-8,9-Dihydro-9-(3,4,5-trimethoxyphenyl)-5,8-methano-1,3-dioxolo(4,5-h) (2)benzoxepin-7(5H)-one (5α,8α,9α) (XVIIIa)

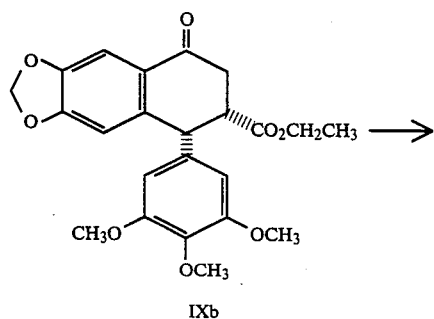

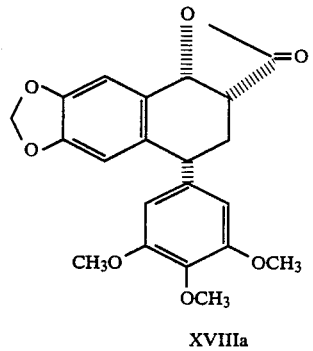

To a solution of the cis-aryltetralone XVIb (124 mg, 0.29 mM) in 10 ml of dry tetrahydrofuran was added 0.29 ml of 2.0M LiBH$_4$ in tetrahydrofuran (0.58 mM). After stirring at room temperature for 17 hours, the reaction mixture was treated with 7 ml of a saturated NH$_4$Cl solution and the solvent layers were separated. The aqueous layer was further extracted with ether (3×5 ml), and the combined organic extract was dried (MgSO$_4$) and concentrated to a light yellow oil. This oil was further purified by preparative thin-layer chromatography using 5% methanol in methylene chloride as eluting solvent. The appropriate fraction at about R$_f$=0.53 was collected, filtered and concentrated to yield the title compound as an oil; TLC [silica/methanol:methylene chloride (5:95)] gave R$_f$=0.53.

$^1$H NMR (CDCl$_3$, δ): 2.33(d, 1H, 11.5 Hz), 2.82(m, 1H), 3.03(t, 1H, 4.9 Hz), 3.79(s, 6H), 3.85(s, 3H), 4.36(d, 1H, 4.5 Hz), 5.24(d, 1H, 5.2 Hz), 5.94(bd, 2H), 6.30(s, 2H), 6.48(s, 1H), 6.75(s, 1H).

EXAMPLE 20 dl-[3aβ,4α,5α,10bβ]-Ethyl 3a,4,5,10b-tetrahydro-3-bromo-5-(3,4,5-trimethoxyphenyl)-1,3-dioxolo(6,7)napth(2,1-d)isoxazole-4-carboxylate (Xa)

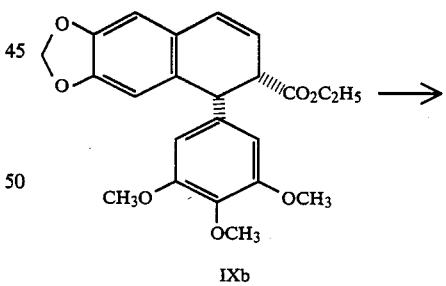

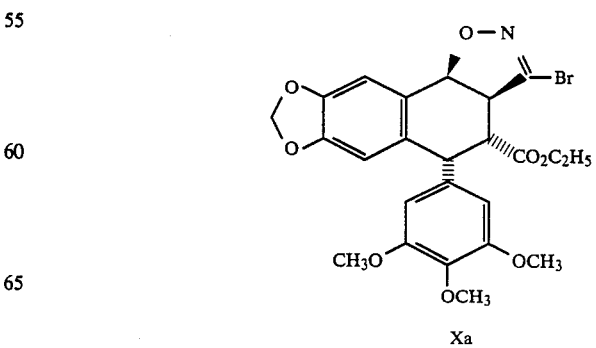

A. Dibromoformaldoxime

To glyoxylic acid oxime hydrate (12 g, 112 mM) in water (60 ml) was added under stirring and ice bath temperature (0°-4° C.) methylene chloride (130 ml) and sodium bicarbonate (18.83 g, 224 mM). To this two-phase mixture was added bromine (35.84 g, 488 mmoles) in methylene chloride (50 ml), and stirring was continued for 7 hours (at 0° C.) followed by additional stirring at room temperature for 13 hours. Excess bromine was destroyed by careful addition of solid sodium thiosulfate. The organic layer was separated and the aqueous layer further extracted with methylene chloride (2×100 ml). The combined organic extract was dried ($Na_2SO_4$) and evaporated to afford the title product as a white solid (11.4 g, 50.13% yield). A portion of this material was recrystallized from Skellysolve B to obtain an analytical sample; m.p. 65°-68° C.

IR (KBr): 3000-3600, 1580 and 980 $cm^{-1}$.

Anal. Calc'd for $CHNOBr_2$: C, 5.91; H, 0.49; N, 6.90

Found: C, 5.40; H, 0.20; N, 6.95

B. dl-[3aβ,4α,5α,10bβ]-Ethyl 3a,4,5,10b-tetrahydro-3-bromo-5-(3,4,5-trimethoxyphenyl)-1,3-dioxolo(6,7)napth(2,1-d)isoxazole-4-carboxylate (Xa)

To a solution of cis-olefin IXb (0.10 g, 0.24 mM) in acetone was added dibromoformaldoxime (146 mg, 0.72 mM) [prepared in Step A] followed by $KHCO_3$ (145 mg, 1.45 mM). The solution was refluxed at 56° C. for 3 hours. Thin-layer chromatography [ether:Skellysolve B (1:1)] indicated that almost all of the starting material ($R_f$=0.30) was consumed and the product spot at $R_f$=0.19 had appeared. The solution was cooled, the solids were filtered off and washed with methylene chloride. The filtrate was concentrated to a yellow oily solid. Pure product (72 mg) was obtained by silica gel column chromatography using 4% ethyl acetate in methylene chloride as the eluting solvent. Recrystallization from ethanol afforded the title compound as a crystalline solid; m.p. 212°-214° C. (dec.).

Anal. Calc'd for $C_{24}H_{24}NO_8Br$: C, 53.95; H, 4.53; N, 2.62

Found: C, 53.64; H, 4.52; N, 2.91

$^1H$ NMR ($CDCl_3$, δ): 1.19(t, 3H, 7.2 Hz), 3.14(dd, 1H, 4.9 Hz, 10.7 Hz), 3.76(s, 6H), 3.81(s, 3H), 3.93(t, 1H, 10.3 Hz), 4.10(q, 2H), 4.37(d, 1H, 4.9 Hz), 5.71(d, 1H, 9.7 Hz), 5.98(s, 2H), 6.08(s, 2H), 6.57(s, 1H), 7.02(s, 1H).

IR (KBr), νmax, $cm^{-1}$: 1732, 1590, 1495, 1482, 1235, 1120.

EXAMPLE 21 dl-[3aβ,4α,5α,10bβ]-Benzhydryl 3a,4,5,10b-tetrahydro-3-bromo-5-(3,4,5-trimethoxyphenyl)-1,3-dioxolo(6,7)napth(2,1-d)isoxazole-4-carboxylate (Xb)

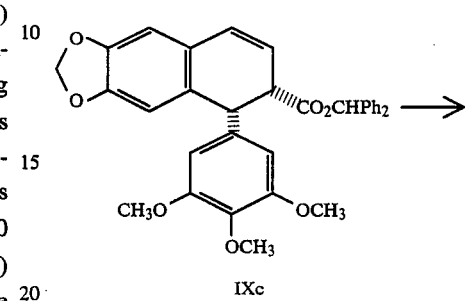

IXc

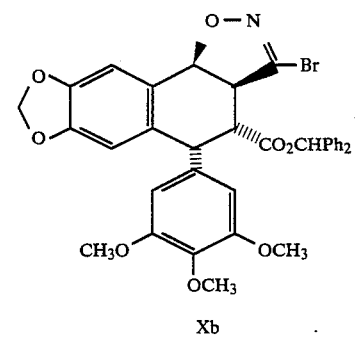

Xb

To a solution of cis-olefin IXc (0.85 g, 1.54 mM) in ethyl acetate (40 ml) was added dibromoformaldoxime (0.94 g, 4.63 mM), followed by $KHCO_3$ (0.47 g, 4.69 mM). The suspension was refluxed for 3 hours. Thin-layer chromatography [ether:Skellysolve B (1:1)] revealed that the reaction was approximately 60% complete. Consequently, additional dibromoformaldoxime (0.47 g) and $KHCO_3$ (0.24 g) were added to the reaction mixture, and the solution was further refluxed for 2.5 hours. The solution was cooled and concentrated to an oil, which was partitioned between methylene chloride and water. The aqueous layer was further extracted with methylene chloride, and the combined organic extract was dried ($MgSO_4$) and concentrated to an oil. The title compound (0.61 g, $R_f$=0.25) was obtained as a solid by silica gel column chromatography of the above oil using 1-3% ethyl acetate in methylene chloride as eluting solvent. An analytical sample was obtained by trituration with ethanol; m.p. 164.5°-168° C.

Anal. Calc'd for $C_{35}H_{30}NO_8Br$: C, 62.50; H, 4.50; N, 2.08; Br, 11.88

Found: C, 62.12; H, 4.45; N, 2.08; Br, 10.75

$^1H$ NMR ($CDCl_3$, δ): 3.30(dd, 1H, 4.7 Hz, 9.4 Hz), 3.44(s, 6H), 3.76(s, 3H), 3.96(t, 1H, 9.7 Hz), 4.34(d, 1H, 4.7 Hz), 5.69(d, 1H, 10.1 Hz), 5.95(s, 2H), 5.98(d, 2H), 6.57(s, 1H), 6.93(s, 1H), 7.01(s, 1H), 7.39-7.12(m, 10H).

IR (KBr), νmax, $cm^{-1}$: 1750, 1590, 1502, 1483, 1240, 1130.

EXAMPLE 22 dl-[3aα,4β,5α,10bα]-Ethyl 3a,4,5,10b-tetrahydro-3-bromo-5-(3,4,5-trimethoxyphenyl)-1,3-dioxolo(6,7)napth(2,1-d)isoxazole-4-carboxylate (XXI)

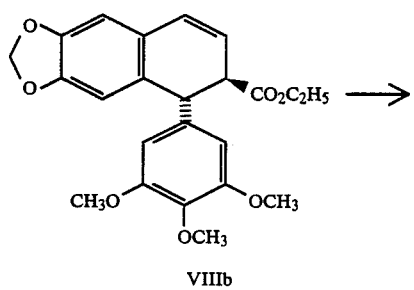

VIIIb

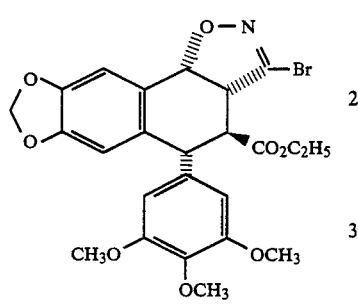

XXI

To a solution of trans-olefin VIIIb (100 mg, 0.24 mM) in ethyl acetate (5 ml) was added dibromoformaldoxime (148 mg, 0.73 mM), followed by KHCO₃ (145 mg, 1.45 mM) and water (2 drops). The reaction mixture was stirred at room temperature for 18 hours. Thin-layer chromatography (5% ethyl acetate in methylene chloride) revealed that all of the starting material ($R_f$=0.71) was consumed and two new spots at $R_f$'s=0.57 and 0.90 had appeared. The reaction mixture was filtered, and the solid precipitates were washed with ethyl acetate. The filtrate was dried (MgSO₄) and concentrated to a solid residue. The desired product ($R_f$=0.57) was obtained by silica gel column chromatography using methylene chloride and 10% ethyl acetate in methylene chloride as eluting solvents, as an amorphous solid (80 mg); m.p. 208°–209° C. (dec.). An analytical sample of the title compound was obtained by recrystallization from 95% ethanol; m.p. 212°–214° C. (dec.).

Anal. Calc'd for C₂₄H₂₄NO₈Br: C, 53.95; H, 4.53; N, 2.62

Found: C, 53.95; H, 4.48; N, 2.58

¹H NMR (CDCl₃, δ): 1.04(t, 3H, 7.2 Hz), 3.12(t, 1H, 8.1 Hz), 3.80(s, 6H), 3.84(s, 3H), 4.08–3.92(m, 3H), 4.17(d, 1H, 8.1 Hz), 5.62(d, 1H, 10.1 Hz), 5.97(s, 2H), 6.31(s, 2H), 6.37(s, 1H), 6.95(s, 1H).

IR (KBr), νmax, cm⁻¹: 1735, 1585, 1498, 1480, 1245, 1120.

EXAMPLE 23 dl-[3aβ,4α,5α,10bβ]-3a,4,5,10b-tetrahydro-3-chloro-5-(3,4,5-trimethoxyphenyl)-1,3-dioxolo(6,7)napth(2,1-d)isoxazole-4-carboxylic acid (Xc)

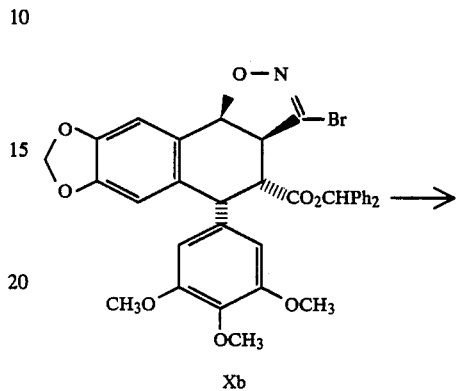

Xb

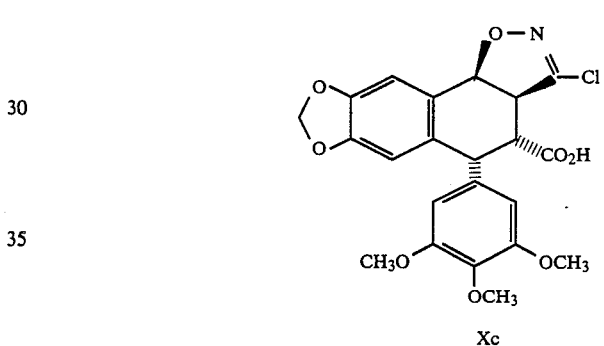

Xc

To a solution of ester Xb (0.41 g, 0.61 mM) in nitromethane (12 ml) was added at room temperature 1N HCl (3.5 ml in nitromethane). The solution was stirred at room temperature for 3 hours and at ice-bath temperature for 30 minutes. The cold solution was filtered to collect the title compound as a white crystalline solid (175 mg); m.p. 238.5° C.

Anal. Calc'd for C₂₂H₂₀NO₈Cl: C, 57.21; H, 4.36; N, 3.03

Found: C, 57.13; H, 4.39; N, 3.18

¹H NMR (CHCl₃, δ): 3.24(dd, 1H, 4.9 Hz, 11.0 Hz), 3.74(s, 6H), 3.80(s, 3H), 3.86(t, 1H, 10.7 Hz), 4.42(d, 1H, 4.7 Hz), 5.76(d, 1H, 9.8 Hz), 5.98(s, 2H), 6.12(s, 2H), 6.58(s, 1H), 7.02(s, 1H).

IR (KBr), νmax, cm⁻¹: 2800–1300, 1715, 1520, 1485, 1230, 1125, 1035.

EXAMPLE 24 dl-[3aβ,4α,5α,10bβ]-3a,4,5,10b-tetrahydro-3-bromo-5-(3,4,5-trimethoxyphenyl)-1,3-dioxolo(6,7)napth(2,1-d)isoxazole-4-carboxylic acid (Xd)

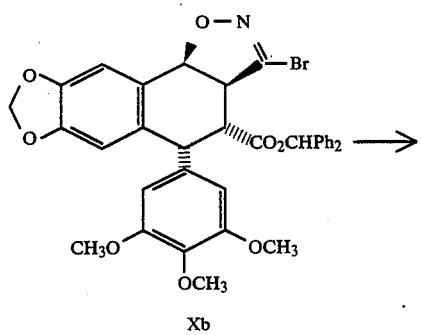

Xb

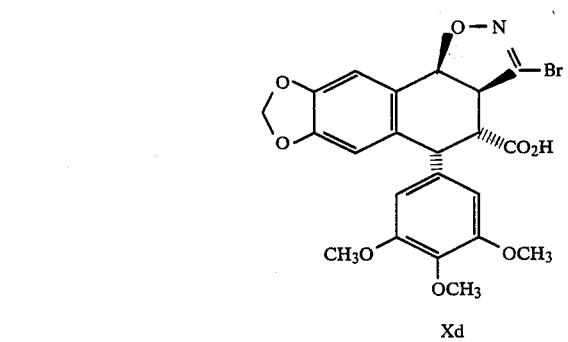

Xd

A cold (0° C.) solution of the ester Xb (134 mg, 0.2 mM) in 1.3 ml of trifluoroacetic acid was allowed to warm to room temperature. After 2 hours of stirring, the trifluoroacetic acid was removed under reduced pressure at about 35° C. The residue was treated with water and filtered to yield the title compound. A portion of the solid was purified by silica gel chromatography using 10% methanol in methylene chloride as the eluting solvent to afford the title compound (42 mg) as a crystalline solid; m.p. 225°-229° C.

EXAMPLE 25 dl-[1α,2α,3β,4β]-1,2,3,4-Tetrahydro-3-cyano-4-hydroxy-1-(3,4,5-trimethoxyphenyl)naphthalene-2-carboxylic acid (XIg)

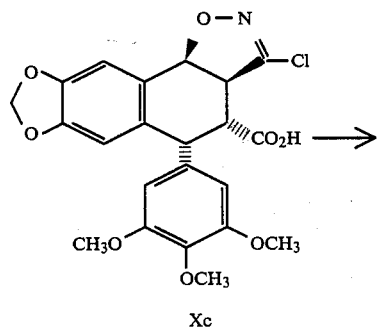

Xc

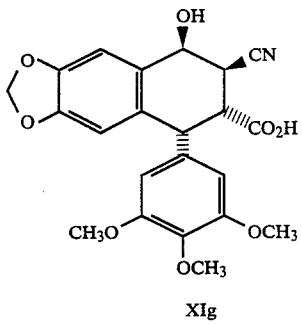

XIg

To a suspension of chloroisoxazoline acid Xc (2.00 g, 0.43 mM) in methanol (100 ml) was added Raney nickel (about 0.5 cc), and the suspension was shaken on a Parr apparatus under 42 psi hydrogen pressure for 4 hours. Platinum oxide (50 mg) was added to the solution and shaking continued on the hydrogenator for an additional 2.5 hours. The catalysts were filtered off through a diatomaceous earth pad and the filtrate concentrated to a solid residue (2 g). Thin-layer chromatography (20% methanol in methylene chloride) of the solid residue revealed besides the starting acid ($R_f$=0.53) two additional components at $R_f$=0.30 (major) and $R_f$=0.09 (minor). The major component at $R_f$=0.30 was isolated as a white solid (0.9 g) by silica gel column chromatography using methanol-methylene chloride (1:5) as eluting solvent. Recrystallization from methanol afforded an analytical sample of the title compound; m.p. 245°-246.5° C. (dec.).

Anal. Calc'd for $C_{22}H_{21}NO_8$: C, 61.82; H, 4.95; N, 3.28

Found: C, 61.67; H, 4.94; N, 3.27

$^1H$ NMR (CDCl$_3$, δ): 3.35(dd, 1H, 3.4 Hz, 12.4 Hz), 3.71(dd, 1H, 12.5 Hz, 5.8 Hz), 3.74(s, 6H), 3.78(s, 3H), 4.55(d, 1H, 5.7 Hz), 4.98(d, 1H, 3.2 Hz), 5.94(m, 2H), 6.11(s, 2H), 6.41(s, 1H), 6.86(s, 1H).

IR (KBr), νmax, cm$^{-1}$: 3490, 2920, 2240, 1750, 1590, 1500, 1485, 1240, 1130, 1035.

EXAMPLE 26 dl-[1α,2α,3β,4β]-1,2,3,4-Tetrahydro-3-cyano-4-hydroxy-1-(3,4,5-trimethoxyphenyl)naphthalene-2-carboxylic acid (XIg)

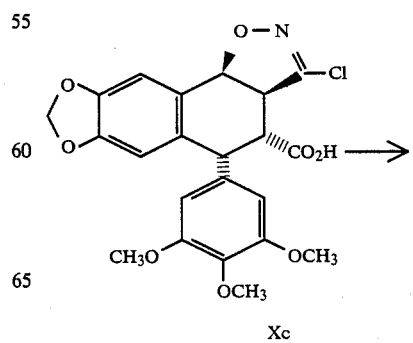

Xc

-continued

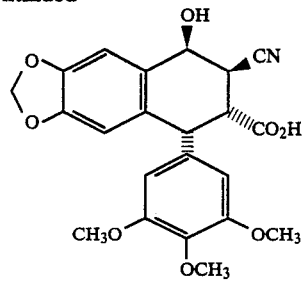

XIg

Raney nickel (about 1.0 cc) was added to a suspension of chloroisoxazoline acid Xc (1.40 g, 3.23 mM) in methanol (200 ml), and the suspension was hydrogenated on a Parr apparatus under an initial hydrogen pressure of 50 psi for 2 hours. The catalyst was filtered off through diatomaceous earth and the solvent evaporated under reduced pressure. The aqueous solution was acidified with 6N HCl and extracted with 10% methanol in methylene chloride. The combined organic extract was dried (MgSO$_4$) and evaporated to yield the title compound as an amorphous solid (0.8 g, 60%), whose $^1$H NMR spectrum was identical to the product produced in Example 25.

EXAMPLE 27 dl-[1α,2α,3β,4β]-Ethyl 1,2,3,4-tetrahydro-3-cyano-4-hydroxy-1-(3,4,5-trimethoxyphenyl)naphthalene-2-carboxylate (XIh)

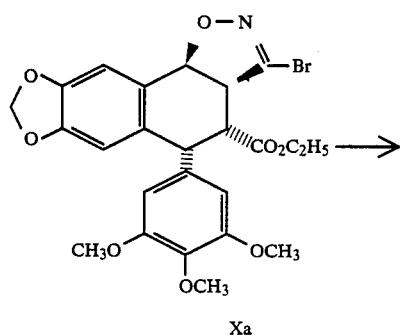

To a suspension of ester Xa (0.106 g, 0.2 mM) in ethyl acetate saturated with water (20 ml) and methanol (5 ml) was added boric acid (36 mg, 0.6 mM) followed by Raney nickel (about 0.1 cc). The suspension was hydrogenated in a Parr apparatus at 40 psi for 6 hours. Thin-layer chromatography (5% ethyl acetate in methylene chloride) revealed, besides the starting ester Xa ($R_f$=0.61), a new component at $R_f$=0.15. The catalyst was filtered off, and the filtrate was concentrated to a solid residue. Silica gel column chromatography of this residue, using 5% and 10% ethyl acetate in methylene chloride as eluting solvents, afforded the title compound ($R_f$=0.15) as an amorphous solid (54 mg). Recrystallization from 95% ethanol afforded the title compound; m.p. 215°–216° C.

Anal. Calc'd for $C_{24}H_{25}NO_8$: C, 63.29; H, 5.53; N, 3.08

Found: C, 63.16; H, 5.59; N, 3.02

$^1$H NMR (CDCl$_3$, δ): 1.17(t, 3H, 7.3 Hz), 2.62(d, 1H, 4.4 Hz), 3.44(dd, 1H, 3.3 Hz, 12.4 Hz), 3.74(m, 1H), 3.74(s, 6H), 3.80(s, 3H), 4.06(q, 2H, 7.1 Hz), 4.53(d, 1H, 5.9 Hz), 5.07(t, 1H, 3.8 Hz), 5.97(dd, 2H), 6.03(s, 2H), 6.42(s, 1H), 6.85(s, 1H).

IR (KBr), νmax, cm$^{-1}$: 3560, 2245, 1725, 1590, 1235, 1128.

EXAMPLE 28 dl-[1α,2α,3β,4β]-Ethyl 1,2,3,4-tetrahydro-3-cyano-4-hydroxy-1-(3,4,5-trimethoxyphenyl)napthalene-2-carboxylate (XIh)

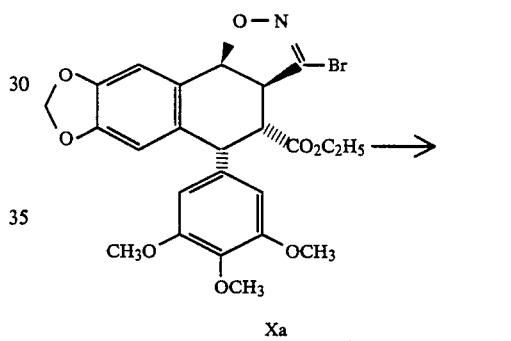

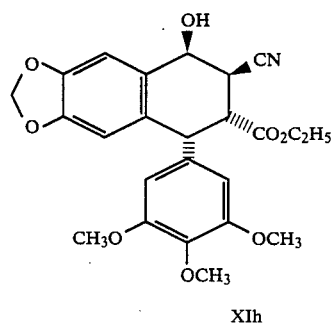

A solution of ester Xa (64 mg, 0.12 mM) in 5 ml of dry benzene under a nitrogen atmosphere was treated with tributyltin hydride (0.12 ml, 0.45 mM) and 2,2'-azobisisobutyronitrile (2 mg). The mixture was heated at reflux temperature for 6 hours and then stirred at room temperature overnight. The reaction mixture was evaporated under reduced pressure and the residue was purified by silica gel column chromatography using 5% and 15% ethyl acetate in methylene chloride as eluting solvent. The appropriate fractions were combined and evaporated under reduced pressure to give the title compound, whose $^1$H NMR spectrum was identical to the product produced in Example 27.

EXAMPLE 29 dl-[1α,2α,3β,4β]-Ethyl 1,2,3,4-tetrahydro-3-cyano-4-hydroxy-1-(3,4,5-trimethoxyphenyl)naphthalene-2-carboxylate (XIh)

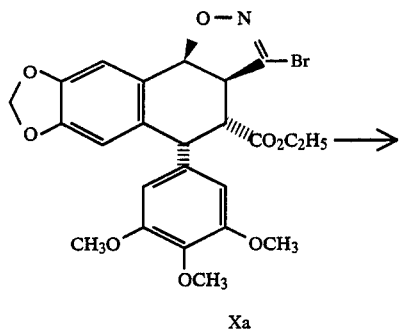

Xa

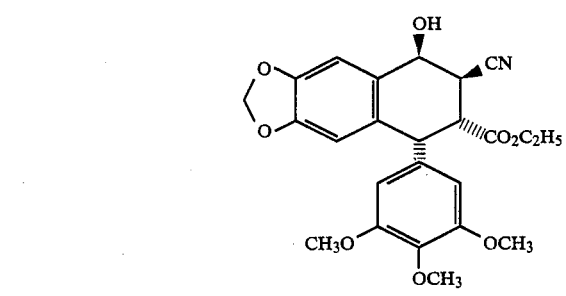

XIh

A suspension of ester Xa (106 mg, 0.2 mM) in 10 ml of 90% aqueous methanol containing 0.08 ml of concentrated HCl and 10 mg of 10% Pd/C (55% by weight in water) was hydrogenated under a hydrogen pressure of 1 atmosphere for 24 hours and then allowed to stand for 5 days. The catalyst was filtered off through diatomaceous earth and the solution was neutralized to about pH 7 with saturated NaHCO₃ solution before the solvent was evaporated under reduced pressure. The residue was purified by silica gel column chromatography using 20% ethyl acetate in methylene chloride as eluting solvent to give 40 mg of the title compound, which was identical to the product produced in Example 27.

EXAMPLE 30 dl-[1α,2α,3β,4β]-1,2,3,4-Tetrahydro-3-cyano-4-hydroxy-1-(3,4,5-trimethoxyphenyl)naphthalene-2-carboxylic acid (XIg)

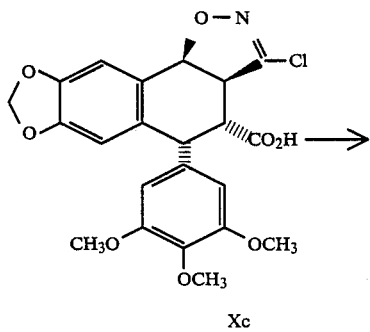

Xc

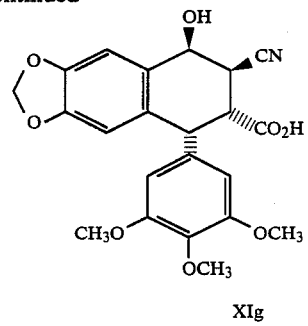

XIg

To a solution of chloroisoxazoline acid Xc (92 mg, 0.2 mM) in 50 ml of solvent (comprising 36 ml of methanol, 10 ml of methylene chloride and 4 ml of water) was added 30 mg of nickel boride, and the mixture was hydrogenated on a Parr apparatus under an initial hydrogen pressure of 40 psi for 16 hours. The catalyst was filtered off through diatomaceous earth and the solvent evaporated under reduced pressure to yield 90 mg of the title compound, which was identical to the product produced in Example 25.

EXAMPLE 31 dl-[1α,2α,3β,4β]-1,2,3,4-Tetrahydro-3-aminomethyl-4-hydroxy-1-(3,4,5-trimethoxyphenyl)naphthalene-2-carboxylic acid (XIi)

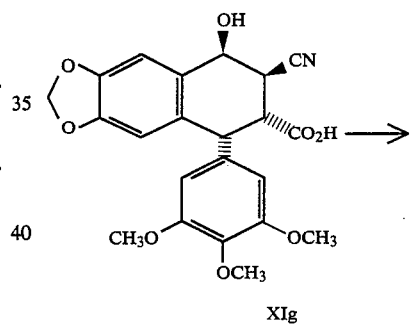

XIg

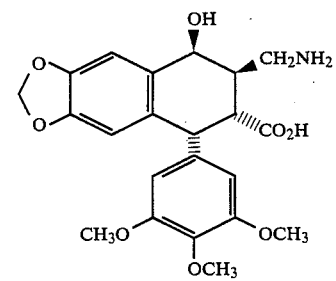

XIi

A solution of the hydroxynitrile XIg (0.50 g, 1.2 mM) in dry tetrahydrofuran (15 ml) was added under nitrogen at 0° C. to a stirred suspension of lithium aluminum hydride (0.16 g, 4.2 mM) in tetrahydrofuran (20 ml). After 16 hours at room temperature, the excess lithium aluminum hydride was decomposed by sequential addition of water (0.16 ml), 15% sodium hydroxide solution (0.16 ml) and water (0.48 ml). The precipitate was filtered off and the tetrahydrofuran was removed under reduced pressure. The aqueous solution was acidified to pH 6 with 0.1N HCl and extracted with methylene chloride. The combined extract was dried (MgSO₄) and evaporated to yield the title compound (0.12 g, 24%). A portion of this sample was dissolved in methanol-methylene chloride (1:4) and applied to a solid phase extraction cartridge of silica. The column was washed with methanol (4 ml) and the amino acid eluted with 10% acetic acid in methanol (2 ml). The solvent was evaporated and the resulting solid dried under high vacuum at 78° C. to give the title compound as an acetic acid salt.

Anal. Calc'd for $C_{22}H_{25}NO_8CH_3COOH\cdot H_2O$: C, 56.57; H, 6.13; N, 2.75

Found: C, 56.85; H, 6.28; N, 2.68

¹H NMR (CHCl₃, δ): 6.84(s, 1H), 6.32(s, 1H), 6.05(s, 2H), 5.88(d, 2H), 4.86(bp, 1H), 4.10(bp, 1H), 3.79(s, 3H), 3.73(s, 6H), 3.26(bp, 2H), 3.13(m, 1H), 2.60(m, 1H), 2.30(m, 1H).

EXAMPLE 32 dl-Epipodophyllotoxin (I)

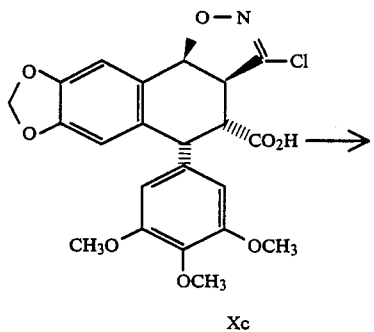

Xc

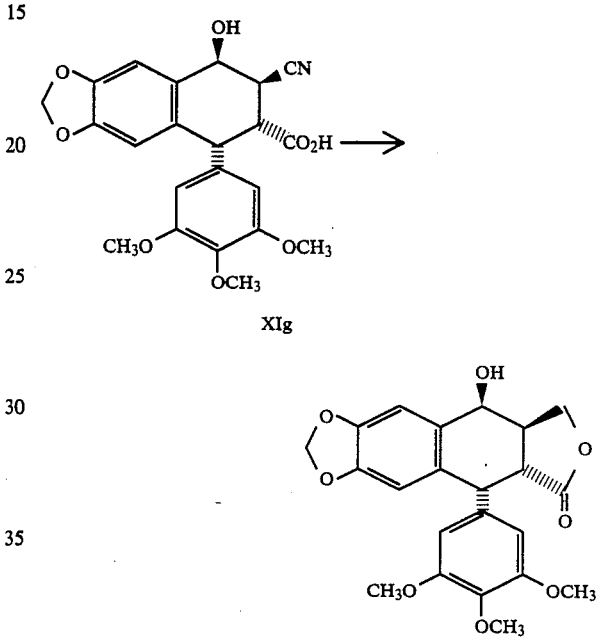

To a solution of chloroisoxazoline acid Xc (200 mg, 0.43 mM) in 100 ml of CH₃OH/H₂O/CH₂Cl₂ (7:1:3) was added nickel boride (60 mg, 0.86 mM), and the suspension was subjected to hydrogenation in a Parr apparatus at 40 psi hydrogen pressure for 18 hours. Platinum oxide (200 mg, 0.88 mM) was added to the solution, and the suspension was further hydrogenated at 40 psi for 2 hours. Thin-layer chromatography (5% MeOH in CH₂Cl₂) indicated the disappearance of the starting acid (R$_f$=0.48) and the appearance of a highly polar component (R$_f$=0.07). The catalysts were filtered off on a diatomaceous earth pad, and the filtrate was concentrated to a syrup. The syrup was dissolved in 50% acetic acid (7 ml), and to the resulting solution was added sodium nitrite (200 mg, 2.9 mM) solution in water (8 ml). After stirring the solution at room temperature for 4 hours, saturated aqueous sodium bicarbonate solution (20 ml) was carefully added, and the reaction solution was extracted with methylene chloride (5×30 ml). The combined organic extract was dried (Na₂SO₄), filtered and concentrated to give the title compound as a light yellow solid (84 mg) which was homogenous on thin-layer chromatography.

¹H NMR (CDCl₃, δ): 2.86(m, 1H), 3.29(dd, 1H, 5.1 Hz, 14.1 Hz), 3.75(s, 6H), 3.81(s, 3H), 4.38(m, 2H), 4.63(d, 1H, 5.1 Hz), 4.88(t, 1H, 3.4 Hz), 6.00(d, 2H), 6.29(s, 2H), 6.56(s, 1H), 6.89(s, 1H).

The above spectral data is in agreement with the data for epipodophyllotoxin reported in J. Med. Chem. 22, 215 (1979).

EXAMPLE 33 dl-Epipodophyllotoxin (I)

A solution of the hydroxynitrile XIg (0.25 g, 0.59 mM) in dry tetrahydrofuran (7 ml) was added under nitrogen to a cooled solution of lithium aluminum hydride (0.08 g, 2 mM) in tetrahydrofuran (20 ml). The reaction mixture was stirred for 16 hours at room temperature. The reaction was terminated by adding 1:1 (v/v) acetic acid in water (10 ml), and the tetrahydrofuran was removed under reduced pressure. A solution of sodium nitrite (200 mg, 2.9 mM) in water (1 ml) was added to the residue and stirred at room temperature for 1 hour. Saturated aqueous NaHCO₃ solution was added to neutralize the acidic solution, and the mixture was then extracted with methylene chloride. The combined organic extract was dried (MgSO₄) and evaporated to yield epipodophyllotoxin (I) (0.21 g, 87%) as a light-brown foam; the ¹H NMR spectrum was identical to the epipodophyllotoxin prepared in Example 32.

EXAMPLE 34

When the general procedure of Examples 1, 2, 10, 11, 17, 20, 23 and 32 are sequentially repeated, except that the starting material 3,4,5-trimethoxy-3',4'-methylenedioxy chalcone XXIIa utilized in Example 1 is replaced by an equimolar amount of a compound of the formula

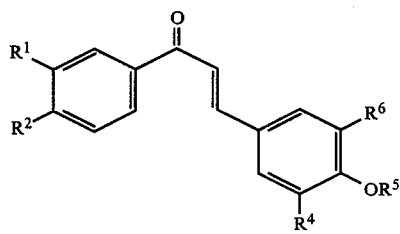

XXIIb-XXIIg wherein

| Compound | R¹ | R² | R⁴ | R⁵ | R⁶ | |
|---|---|---|---|---|---|---|
| XXIIb | H | OCH | H | CH₃ | H | |
| XXIIc | H | OCH₃ | OCH₃ | CH₃ | H | |
| XXIId | OCH₃ | OCH₃ | H | CH₃ | H | |
| XXIIe | OCH₃ | OCH₃ | OCH₃ | CH₃ | H | |
| XXIIf | —OCH₂O— | | OCH₃ | CH₃ | H | and |
| XXIIg | OCH₃ | H | H | CH₃ | H, | respectively |

[which are prepared by the general procedures described in *Synthesis*, 647–650 (1980)], there is thereby produced a compound of the formula

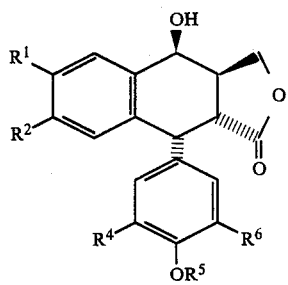

XIIb-XIIg wherein

| Compound | R¹ | R² | R⁴ | R⁵ | R⁶ | |
|---|---|---|---|---|---|---|
| XIIb | H | OCH₃ | H | CH₃ | H | |
| XIIc | H | OCH₃ | OCH₃ | CH₃ | H | |
| XIId | OCH₃ | OCH₃ | H | CH₃ | H | |
| XIIe | OCH₃ | OCH₃ | OCH₃ | CH₃ | H | |
| XIIf | —OCH₂O— | | OCH₃ | CH₃ | H | and |
| XIIg | OCH₃ | H | H | CH₃ | H, | respectively. |

We claim:

1. A compound of the formula

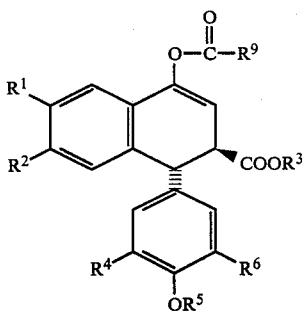

XIV wherein
R¹ and R² each are independently hydrogen or (lower)alkoxy, or R¹ and R², taken together, is methylenedioxy;
R³ is hydrogen or a carboxyl-protecting group;
R⁴ and R⁶ each are independently hydrogen or (lower)alkoxy;
R⁵ is hydrogen or a phenol-protecting group; and
R⁹ is phenyl or (lower)alkyl optionally substituted by one or more halogen atoms selected from fluorine, chlorine and bromine.

2. A compound of claim 1 having the formula

XIVa wherein R³ is hydrogen or a carboxyl-protecting group;
R⁵ is hydrogen or a phenol-protecting group; and
R⁹ is phenyl or (lower)alkyl optionally substituted by one or more halogen atoms selected from fluorine, chlorine and bromine.

3. The compound of claim 2 wherein R³ is diphenylmethyl; R⁵ is methyl; and R⁹ is methyl.

* * * * *